US012649035B2

(12) United States Patent
  Tarakci et al.

(10) Patent No.:  US 12,649,035 B2
(45) Date of Patent:      Jun. 9, 2026

(54) METHODS AND APPARATUS FOR ACOUSTIC MONITORING OF RESPIRATORY THERAPY DEVICES

(71) Applicant: ResMed Pty Ltd, Bella Vista (AU)

(72) Inventors: Cem Tarakci, Sydney (AU); Barton John Kenyon, Sydney (AU); Aniket Sharma, Sydney (AU); Timothy Nicholas Shadie, Sydney (AU)

(73) Assignee: ResMed Pty Ltd (AU)

( * ) Notice:  Subject to any disclaimer, the term of this patent is extended or adjusted under 35 U.S.C. 154(b) by 670 days.

(21) Appl. No.:  18/043,590

(22) PCT Filed:  Sep. 7, 2021

(86) PCT No.:  PCT/AU2021/051035
  § 371 (c)(1),
  (2) Date:  Mar. 1, 2023

(87) PCT Pub. No.:  WO2022/051801
  PCT Pub. Date: Mar. 17, 2022

(65)  Prior Publication Data
  US 2023/0310770 A1      Oct. 5, 2023

Related U.S. Application Data

(60) Provisional application No. 62/706,809, filed on Sep. 11, 2020.

(51) Int. Cl.
  *A61M 16/00*      (2006.01)
  *A61B 5/00*      (2006.01)
  (Continued)

(52) U.S. Cl.
  CPC .... *A61M 16/0003* (2014.02); *A61M 16/0051* (2013.01); *A61M 16/024* (2017.08);
  (Continued)

(58) Field of Classification Search
  CPC .......... A61M 16/0003; A61M 16/0051; A61M 16/024; A61M 16/0066; A61M 16/0069;
  (Continued)

(56)  References Cited

U.S. PATENT DOCUMENTS 4,944,310  A      7/1990  Sullivan
  6,526,831  B2      3/2003  Ben-Romdhane
  (Continued)

FOREIGN PATENT DOCUMENTS

EP      3505080 A1      7/2019
  EP      2932340 B1      12/2019
  (Continued)

OTHER PUBLICATIONS

Extended European Search Report in EP Application No. 21865383.0, Mailed Aug. 5, 2024. 9 Pages.
  (Continued)

*Primary Examiner* — Joseph D. Boecker
(74) *Attorney, Agent, or Firm* — Botos Churchill IP Law LLP

(57)  ABSTRACT

Systems and methods implement a status assessment of a respiratory device with sound evaluation. In some versions, the system may include a motor operated pressure generator to generate airflow through an air circuit to a patient interface. The system may include a transducer producing a signal representing sound of the generator in the circuit. The system may include a controller, such as with a processor, for generator control. The system, such as with the controller, computes a sound representation in the frequency domain. The system applies, to the frequency domain representation, any one or more of an integer-multiple function, non-integer-multiple function, a statistical correlation function and resonant frequency function, such as of a fundamental frequency attributable to motor operation. The sys-
  (Continued)

tem may derive a noise vector with data from the function (s). The system may classify the vector to obtain a status indicator of the generator and generate indicator related output.

47 Claims, 14 Drawing Sheets

(51) Int. Cl.

| | | |
|---|---|---|
| *A61B 5/08* | (2006.01) | |
| *A61B 5/087* | (2006.01) | |
| *A61M 16/06* | (2006.01) | |
| *G16H 40/63* | (2018.01) | |

(52) U.S. Cl.
CPC .......... *A61M 16/026* (2017.08); *G16H 40/63* (2018.01); *A61B 5/0816* (2013.01); *A61B 5/0826* (2013.01); *A61B 5/087* (2013.01); *A61B 5/4818* (2013.01); *A61B 5/7257* (2013.01); *A61M 16/0069* (2014.02); *A61M 16/06* (2013.01); *A61M 2205/3375* (2013.01); *A61M 2205/70* (2013.01)

(58) Field of Classification Search
CPC .......... A61M 16/06; A61M 2205/3375; A61M 2205/70; A61M 2205/702; G16H 40/63; A61B 5/0816; A61B 5/0826; A61B 5/087; A61B 5/4818; A61B 5/7257; F04D 27/001; F04D 27/008
See application file for complete search history.

(56) References Cited

U.S. PATENT DOCUMENTS

| | | | |
|---|---|---|---|
| 6,532,959 | B1 | 3/2003 | Berthon-Jones |
| 6,885,972 | B2 | 4/2005 | Samata et al. |
| 7,069,154 | B2 | 6/2006 | Orkisz |
| 7,430,257 | B1 | 9/2008 | Shattil |
| 7,453,224 | B2 | 11/2008 | Sullivan |
| 7,866,944 | B2 | 1/2011 | Kenyon et al. |
| 7,891,354 | B2 | 2/2011 | Farbarik |
| 8,028,583 | B2 | 10/2011 | Attia et al. |
| 8,636,479 | B2 | 1/2014 | Kenyon et al. |
| 8,638,014 | B2 | 1/2014 | Sears |
| 9,071,110 | B2 | 6/2015 | Lalonge et al. |
| 9,289,548 | B2 | 3/2016 | Kalt et al. |
| 9,597,469 | B2 | 3/2017 | Colla et al. |
| 10,006,462 | B2 | 6/2018 | Becerra et al. |

| | | | | |
|---|---|---|---|---|
| 10,141,882 | B2 | 11/2018 | Favreau | |
| 10,145,761 | B1 | 12/2018 | Jenkins et al. | |
| 10,175,300 | B2 | 1/2019 | Armitstead et al. | |
| 10,207,040 | B2 | 2/2019 | Tarn et al. | |
| 10,343,689 | B2 | 7/2019 | Kwon | |
| 11,123,507 | B2 | 9/2021 | Holley et al. | |
| 2006/0135907 | A1 | 6/2006 | Remde et al. | |
| 2008/0078248 | A1* | 4/2008 | Farbarik | A61M 16/0051 |
| | | | | 73/613 |
| 2011/0313689 | A1* | 12/2011 | Holley | A61M 16/0069 |
| | | | | 702/56 |
| 2019/0240402 | A1 | 8/2019 | Consiglio | |
| 2019/0336711 | A1 | 11/2019 | O'Donnell et al. | |
| 2019/0371460 | A1 | 12/2019 | Gutierrez | |
| 2020/0045570 | A1 | 2/2020 | Wolcott et al. | |
| 2020/0054847 | A1* | 2/2020 | Burgess | A61M 16/1005 |
| 2020/0147329 | A1 | 5/2020 | Cappelli et al. | |
| 2020/0158562 | A1 | 5/2020 | Hatakeyama et al. | |
| 2020/0292506 | A1 | 9/2020 | Hayzen et al. | |
| 2020/0398007 | A1 | 12/2020 | Shadie et al. | |
| 2021/0041329 | A1 | 2/2021 | Bowers et al. | |
| 2021/0162838 | A1 | 6/2021 | Thiel | |
| 2021/0273527 | A1 | 9/2021 | Knorr | |

FOREIGN PATENT DOCUMENTS

| | | | |
|---|---|---|---|
| EP | 3662331 | A2 | 6/2020 |
| EP | 3791236 | A1 | 3/2021 |
| EP | 3823247 | A1 | 5/2021 |
| WO | 2010091462 | A1 | 8/2010 |
| WO | 2013020167 | A1 | 2/2013 |
| WO | 2016155270 | A1 | 10/2016 |
| WO | 2018190732 | A2 | 10/2018 |
| WO | 2018190732 | A3 | 11/2018 |
| WO | 2019028269 | A2 | 2/2019 |
| WO | 2019167086 | A1 | 9/2019 |
| WO | 2019216975 | A1 | 11/2019 |
| WO | 2020070349 | A1 | 4/2020 |
| WO | 2020220091 | A1 | 11/2020 |
| WO | 2021062466 | A1 | 4/2021 |
| WO | 2021084501 | A1 | 5/2021 |
| WO | 2021166168 | A1 | 8/2021 |
| WO | 2021207796 | A1 | 10/2021 |

OTHER PUBLICATIONS

West, John B., "Respiratory Physiology", Lippincott Williams & Wilkins, 9th Edition published 2012.
International Search Report and Written Opinion issued in corresponding International Application No. PCT/AU2021/051035, mailed Dec. 10, 2021, 11 pages.

\* cited by examiner

Nasal cavity

Oral cavity

Larynx

Vocal folds

Oesophagus

Trachea

Bronchus

Lung

Heart

Diaphragm

Alveolar sacs

METHODS AND APPARATUS FOR ACOUSTIC MONITORING OF RESPIRATORY THERAPY DEVICES

1 CROSS-REFERENCE TO RELATED APPLICATIONS

The present application is a national phase entry under 35 U.S.C. § 371 of International Application No. PCT/AU2021/051035 filed Sep. 7, 2021 published in English, which claims priority from U.S. Provisional Patent Application No. 62/706,809 filed Sep. 11, 2020, all of which are incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to monitoring medical devices or apparatus.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired CO2 from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Therapy Device (RT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

2.2.3.2 Respiratory Therapy (RT) Device

A respiratory therapy (RT) device may be used individually or as part of a system to deliver one or more of a number of therapies described above, such as by operating the device to generate a flow of air for delivery to an interface to the airways. The flow of air may be pressure-controlled (for respiratory pressure therapies) such as a respiratory pressure therapy device (RPT) or flow-controlled (for flow therapies such as HFT) such as a respiratory flow therapy (RFT) device. Thus, RT devices may act as flow therapy and/or pressure therapy devices. Examples of RPT devices include a CPAP device and a ventilator. Examples of a RFT device may be an HFT device or a portable oxygen concentrator.

2.2.3.3 Air Circuit

An air circuit is a conduit or a tube constructed and arranged to allow, in use, a flow of air to travel between two components of a respiratory therapy system such as the RT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Data Management

There may be clinical reasons to obtain data to determine whether the patient prescribed with respiratory therapy has been "compliant", e.g. that the patient has used their RT device according to one or more "compliance rules". One example of a compliance rule for CPAP therapy is that a patient, in order to be deemed compliant, is required to use the RT device for at least four hours a night for at least 21 of 30 consecutive days. In order to determine a patient's compliance, a provider of the RT device, such as a health care provider, may manually obtain data describing the patient's therapy using the RT device, calculate the usage over a predetermined time period, and compare with the compliance rule. Once the health care provider has determined that the patient has used their RT device according to the compliance rule, the health care provider may notify a third party that the patient is compliant.

There may be other aspects of a patient's therapy that would benefit from communication of therapy data to a third party or external system.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.4 RT Device Monitoring

RT devices such as CPAP devices and ventilators can deteriorate over time and usage. In particular, the blowers in RT devices, or other motor operated pressure source, may become acoustically noisy over time, due to material deterioration, use beyond capacity, use beyond design lifetime, use in extreme operating conditions. Such noise can become uncomfortable for users of RT devices, which may affect their long-term adherence to respiratory therapy. In addition, some of these faults may, if left unaddressed, result in the necessity for service. The noise emitted by blowers is suitable for monitoring purposes since it is correlated with deterioration and may be sensed noninvasively with inexpensive sensors in pneumatic communication with the air path. A user's sense of hearing is particularly unsuited for such a determination as it is typically difficult to distinguish pertinent sound differences and whether or not any are significant or insignificant. Automated systems can be created to provide monitoring to assist with these technical problems associated with the operation of RT devices. However, acoustic monitoring is a difficult technical challenge. For example, acoustic monitoring of blowers is often inaccurate and in particular may result in false indications of deterioration. There is therefore a need to acoustically monitor blowers in RT devices so as to accurately detect deterioration in a timely fashion, in order to maximise user comfort, save servicing costs, and maintain safe operation of the RT device.

3 BRIEF SUMMARY OF THE TECHNOLOGY

The present technology is directed towards monitoring medical devices used in the amelioration, treatment, or prevention of respiratory disorders.

A first aspect of the present technology relates to apparatus and methods used to monitor devices used for the amelioration, treatment or prevention of a respiratory disorder. In particular, the disclosed apparatus acoustically monitors device status. The sound signal generated by an air path microphone is analysed in the Fourier domain to determine device status. The analysis of the Fourier sound spectrum may be in any one or more (e.g., all or fewer (any subgroups)) of four modes: Patterns of peaks at integer multiples of the fundamental frequency (harmonics) that is set by the motor speed; patterns of peaks at non-harmonic frequencies; "bulges" in predetermined frequency ranges; and/or correlation between the spectrum, (e.g., all or one or more portions of it), and one or more previously captured sound spectrum(s). Data of each of these modes may analysed to determine device status.

Some implementations of the present technology may include a respiratory therapy system for treating a respiratory disorder in a patient. The system may include a pressure generator configured to generate a flow of air through an air circuit to a patient interface for treating the respiratory disorder, the pressure generator may include a motor. The system may include a transducer configured to generate a signal representing sound in the air circuit generated by the pressure generator during generation of the flow of air. The system may include a controller configured to control the pressure generator to generate the flow of air. The system may include a controller configured to compute a frequency domain representation of the generated sound signal. The system may include a controller configured to process the frequency domain representation. The system may include a controller configured to apply, to the frequency domain representation, an integer-multiple function of a fundamental frequency attributable to operation of the motor. The system may include a controller configured to apply, to the frequency domain representation, a non-integer-multiple function of the fundamental frequency attributable to operation of the motor.

The system may include a controller configured to apply, to the frequency domain representation and one or more predetermined fault signature spectra, a statistical correlation function. The system may include a controller configured to apply, to the frequency domain representation, a resonant frequency function. The system may include a controller configured to derive a noise vector with output data from the processing of the frequency domain representation, such any one or more of the applied function(s). The system may include a processor configured to classify the noise vector to obtain a status indicator of the pressure generator, such as a component of the pressure generator. The system may include a processor configured to generate an output with or based on the status indicator.

In some implementations, the output data may include values of peak ratios. The controller may be configured to compute at least one peak ratio of the peak ratios by dividing a height of a peak by a power (e.g., average power or root mean square (RMS) power) in a band surrounding the peak. The integer-multiple function may be configured to extract harmonic peak ratios from peaks in the frequency domain representation at integer multiples of the fundamental frequency (which can be understood to be the motor speed). The noise vector may be derived, for the classifying, with output data from the applying of the integer-multiple function. The non-integer-multiple function may be configured to extract non-harmonic peak ratios from peaks in the frequency domain representation at non-integer multiples of the fundamental frequency. The noise vector may be derived, for the classifying, with output data from the applying of the non-integer-multiple function. Each of the integer and non-integer multiple functions may be configured or applied to compare the calculated ratios with respective ratio thresholds. The non-integer-multiple function may be further configured to output location information of the non-harmonic peak ratios. The integer multiple function may be further configured to output location information of the harmonic peak ratios. The controller may be further configured to apply, to the frequency domain representation, a resonant frequency function, and to derive the noise vector with output data from the resonant frequency function. The output data from the resonant frequency function may include power data for one or more predetermined resonant regions. The power data may include a noise ratio. The noise ratio may include an average power of a predetermined resonant region divided by a power of a reference region. The non-integer-multiple function may be further configured to threshold peak ratios using one or more first predetermined ratio threshold(s).

In some implementations, the processor may be further configured to access one or more predetermined fault signature spectra. The processor may be further configured to apply, to the frequency domain representation and the one or more predetermined fault signature spectra, a statistical correlation function. The noise vector may be derived, for the classifying, with output data from the applying of the statistical correlation function. To classify the noise vector, the processor may be configured to compare the output data from the applying of the statistical correlation function to one or more correlation threshold(s).

In some implementations, to classify the noise vector, the processor may be configured to count harmonic peak ratios in the noise vector that exceed one or more second predetermined threshold(s). To classify the noise vector, the processor may be configured to form a weighted sum from harmonic peak ratios generated with the integer-multiple function. The controller may include the processor. The processor may be a processor of a computing device that may be external to the controller. The controller may be configured to communicate the noise vector to the processor. The output generated with or based on the status indicator may include a communication of the status indicator to the controller. The output generated with or based on the status indicator may include at least (i.e., or both) of (a) a presentation on a remote display, and (b) sending a message or instruction to a device external to the controller and/or the processor. The controller may be further configured to control operation of the pressure generator based on the status indicator. The controller may be configured to deactivate the pressure generator based on the status indicator. The controller may be configured to limit operation of the pressure generator based on the status indicator. Optionally, the transducer may be in, or in a fluid communication with, an air flow path of the pressure generator and/or the air circuit.

In some implementations, the controller may be configured to operate the transducer to generate the signal representing sound during the control of the pressure generator by the controller in a therapy mode. The controller may be, for the computing of the frequency domain representation, configured to parse the signal representing sound into a plurality of intervals that each coincide with a period of time of a sub-portion of a respiratory event type. The respiratory event type may include a detected apnea and/or a detected breath cycle. The period of time of the sub-portion of the respiratory event may include a detected interval coinciding with a predetermined blower motor speed that is approximately constant. The controller may be configured to combine the parsed intervals for the computing of the frequency domain representation. The controller may be configured to combine a number of the parsed intervals to at least achieve a minimum quantity. The minimum quantity may comprise a breath count associated with the combined number of the parsed intervals or an accumulated time amount of the combined number of the parsed intervals. The classifier may be configured to classify a weighed sum of integer multiple peak ratios, non-integer multiple peak ratios, and noise ratios. The classifier may be configured to classify each of a weighed sum of integer multiple peak ratios, a weighted sum of non-integer multiple peak ratios, and a weighted sum of noise ratios.

Some implementations of the present technology may include a method, such as by one or more processors, of determining a status of a respiratory therapy system that may include a pressure generator for generating a flow of air through an air circuit to a patient interface. The method may include computing a frequency domain representation of a sound signal representing sound in the air circuit during generation of the flow of air. The method may include processing the frequency domain representation. The method may include applying, to the frequency domain representation, an integer-multiple function of a fundamental frequency attributable to operation of a motor of the pressure generator. The method may include applying, to the frequency domain representation, a non-integer-multiple function of the fundamental frequency attributable to operation of the motor of the pressure generator. The method may include applying, to the frequency domain representation and one or more predetermined fault signature spectra, a statistical correlation function. The method may include applying, to the frequency domain representation, a resonant frequency function. The method may include deriving a noise vector with output data from the processing of the frequency domain representation such as any one or more of the applied functions. The method may include classifying the noise vector to obtain a status indicator of the pressure generator such as a status indicator of at least a component of the pressure generator. The method may include generating an output with or based on the status indicator. In some implementations, the output data sets may include values of peak ratios.

In some implementations, the method may further include computing at least one peak ratio of the peak ratios by dividing a height of a peak by a power (e.g., average power or root mean square (RMS) power) in a band surrounding the peak. The integer-multiple function may extract harmonic peak ratios from peaks in the frequency domain representation at integer multiples of the fundamental frequency. The noise vector may be derived, for the classifying, with output data from the applying of the integer-multiple function. The non-integer-multiple function may extract non-harmonic peak ratios from peaks in the frequency domain representation at non-integer multiples of the fundamental frequency. The noise vector may be derived, for the classifying, with output data from the applying of the non-integer-multiple function. The method may include applying, to the frequency domain representation, a resonant frequency function, and may further include deriving the noise vector with an output data set from the resonant frequency function. The output data set from the resonant frequency function may include power data for one or more predetermined resonant regions. The power data may include a noise ratio. The noise ratio may include an average power of a predetermined resonant region divided by a power of a reference region.

In some implementations, the method may include, such as by a processor or controller, accessing one or more predetermined fault signature spectra. The method may include, such as by a processor or controller, applying, to the frequency domain representation and the one or more predetermined fault signature spectra, a statistical correlation function. The noise vector may be derived, for the classifying, with output data from the applying of the statistical correlation function. The classifying the noise vector comprises comparing the output data from the applying of the statistical correlation function to one or more correlation thresholds.

Applying the non-integer-multiple function may further include thresholding peak ratios using one or more first predetermined ratio thresholds, such as a predetermined ratio threshold. The classifying may include counting harmonic peak ratios in the noise vector that exceed one or more second predetermined thresholds, such as a predetermined threshold. The classifying may include forming a weighted sum from harmonic peak ratios generated with the integer-multiple function. The output generated with or based on the status indicator may include communicating the status indicator to a controller or external device. The output generated with or based on the status indicator may include at least one of (a) output on a display of a remote external device, or (b) output on a display coupled with the pressure generator. The method may include controlling, by a controller, an operation of the pressure generator based on the status indicator. The controller may deactivate the pressure generator based on the status indicator. The controller may limit operation of the pressure generator based on the status indicator.

In some implementations, the method may include a transducer that generates the sound signal during operation of the pressure generator in a therapy mode. The method may include, such as by a controller or processor, parsing, for the computing of the frequency domain representation, the sound signal into a plurality of intervals that each coincide with a period of time of a sub-portion of a respiratory event type, which may be taken from a plurality of consecutive or non-consecutive respiratory events. The respiratory event type may include a detected apnea and/or a detected breath cycle. The period of time of the sub-portion of the respiratory event comprises a detected interval coinciding with a predetermined blower motor speed that is approximately constant. The method may include combining, such as by the processor or controller, the parsed intervals for the computing of the frequency domain representation. The method may include determining, such as by the processor or controller, that the combined parsed intervals at least satisfy a minimum quantity. The minimum quantity may comprise a breath count associated with the combined parsed intervals or an accumulated time amount of the combined parsed intervals. The classifying may evaluate a weighed sum of integer multiple peak ratios, non-integer multiple peak ratios, and noise ratios. The classifying may evaluate each of a weighed sum of integer multiple peak ratios, a weighted sum of non-integer multiple peak ratios, and a weighted sum of noise ratios.

Some apparatus implementations of the present technology may include may include means for generating a flow of air through an air circuit to a patient interface for treating a respiratory disorder in a patient. The apparatus may include means for generating a sound signal representing sound in the air circuit generated by the means for generating during generation of the flow of air. The apparatus may include means for computing a frequency domain representation of the sound signal. The means for processing the frequency domain representation. The means for processing may include any one or more of (a) means for applying, to the frequency domain representation, an integer-multiple function of a fundamental frequency attributable to operation of a motor of the means for generating the flow of air; (b) means for applying, to the frequency domain representation, a non-integer-multiple function of the fundamental frequency attributable to operation of the motor of the means for generating the flow of air, (c) means for applying, to the frequency domain representation and one or more predetermined fault signature spectra, a statistical correlation function, and (d) means for applying, to the frequency domain representation, a resonant frequency function. The apparatus may include means for deriving a noise vector with output data from the means for processing the frequency domain representation, such as from the integer-multiple function and the non-integer-multiple function. The apparatus may include means for classifying the noise vector to obtain a status indicator of at least a component of the means for generating the flow of air. The apparatus may include means for generating an output with or based on the status indicator.

Some implementations of the present technology may include a respiratory therapy system for treating a respiratory disorder in a patient. The system may include a pressure generator configured to generate a flow of air through an air circuit to a patient interface for treating the respiratory disorder. The pressure generator may include a motor. The system may include a transducer configured to generate a signal representing sound in the air circuit generated by the pressure generator during generation of the flow of air. The system may include a controller. The controller may be configured to control the motor of the pressure generator to generate the flow of air. The controller may be configured to compute a frequency domain representation of the generated sound signal. The controller may be configured to apply, to the frequency domain representation, a resonant frequency function. The controller may be configured to derive a noise vector with an output data set from the resonant frequency function. The system may include a processor. The processor may be configured to classify the noise vector to obtain a status indicator of at least a component of the pressure generator. The processor may be configured to generate an output with or based on the status indicator.

In some implementations, the controller may be further configured to apply, to the frequency domain representation, an integer-multiple function of a fundamental frequency attributable to operation of the motor, and may be configured to derive the noise vector with an output data set from the integer multiple function. The controller may be further configured to apply, to the frequency domain representation, a non-integer-multiple function of a fundamental frequency attributable to operation of the motor, and to derive the noise vector with an output data set from the non-integer-multiple function.

Some implementations of the present technology may include a method of determining a status of a respiratory therapy system that may include a pressure generator for generating a flow of air through an air circuit to a patient interface. The method may include computing a frequency domain representation of a sound signal representing sound in the air circuit during generation of the flow of air. The method may include applying, to the frequency domain representation, a resonant frequency function. The method may include deriving a noise vector with an output data set from the resonant frequency function. The method may include classifying the noise vector to obtain a status indicator of at least a component of the pressure generator. The method may include generating an output with or based on the status indicator.

In some implementations, the method may include applying, to the frequency domain representation, an integer-multiple function of a fundamental frequency attributable to operation of a motor of the pressure generator, and further deriving the noise vector with an output data set from the integer-multiple function. The method may include applying, to the frequency domain representation, a non-integer-multiple function of a fundamental frequency attributable to operation of a motor of the pressure generator, and further deriving the noise vector with an output data set from the non-integer multiple function.

Some apparatus implementations of the present technology may include may include means for generating a flow of air through an air circuit to a patient interface for treating a respiratory disorder in a patient. The apparatus may include means for generating a sound signal representing sound in the air circuit generated by the means for generating during generation of the flow of air. The apparatus may include means for computing a frequency domain representation of the sound signal. The apparatus may include means for applying, to the frequency domain representation, a resonant frequency function. The apparatus may include means for deriving a noise vector with an output data set from the resonant frequency function. The apparatus may include means for classifying the noise vector to obtain a status indicator of at least a component the means for generating the flow of air. The apparatus may include means for generating an output with or based on the status indicator.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing or improvement in acoustic monitoring systems for assessment of such devices.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RT device 4000. Air from the RT device 4000 is humidified in a humidifier 5000, and passes along an air circuit 4170 to the patient 1000. A bed partner 1100 is also shown. The patient is sleeping in a supine sleeping position.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows a patient interface in the form of a nasal mask in accordance with one form of the present technology.

4.4 Rt Device

FIG. 4A shows an example RT device in accordance with one form of the present technology.

FIG. 4B is a schematic diagram of an example pneumatic path of an RT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
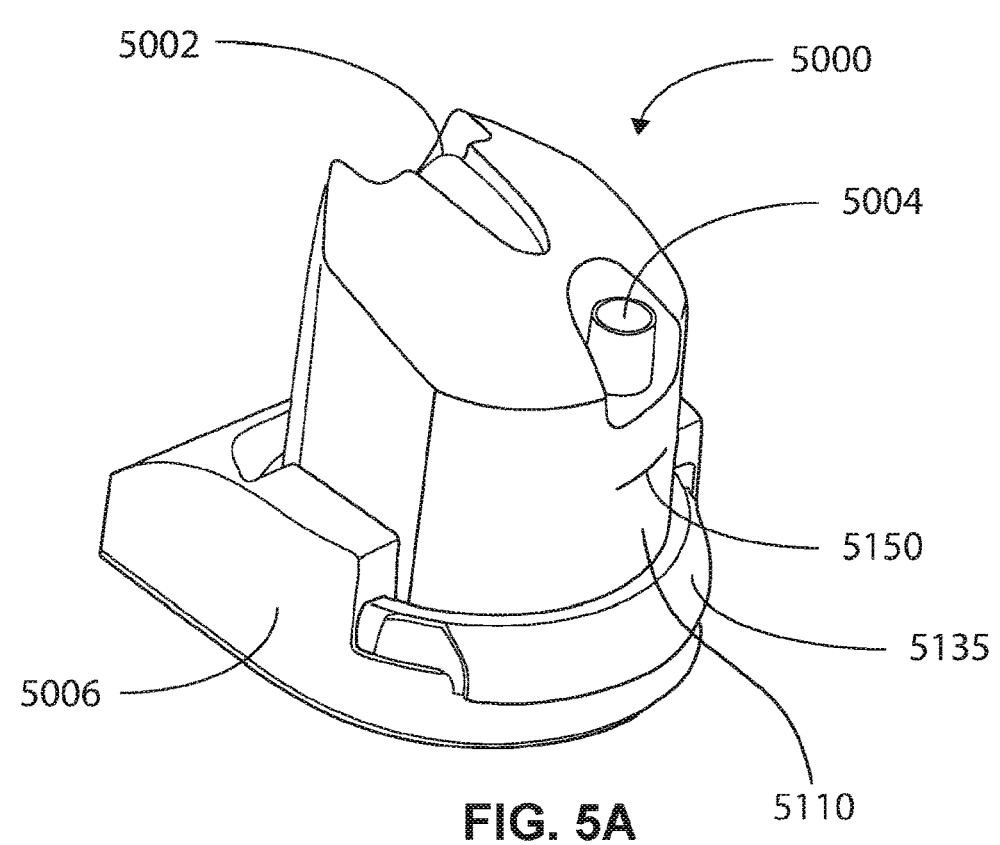

FIG. 5A shows an isometric view of an example humidifier in accordance with one form of the present technology.

Figure 5B:
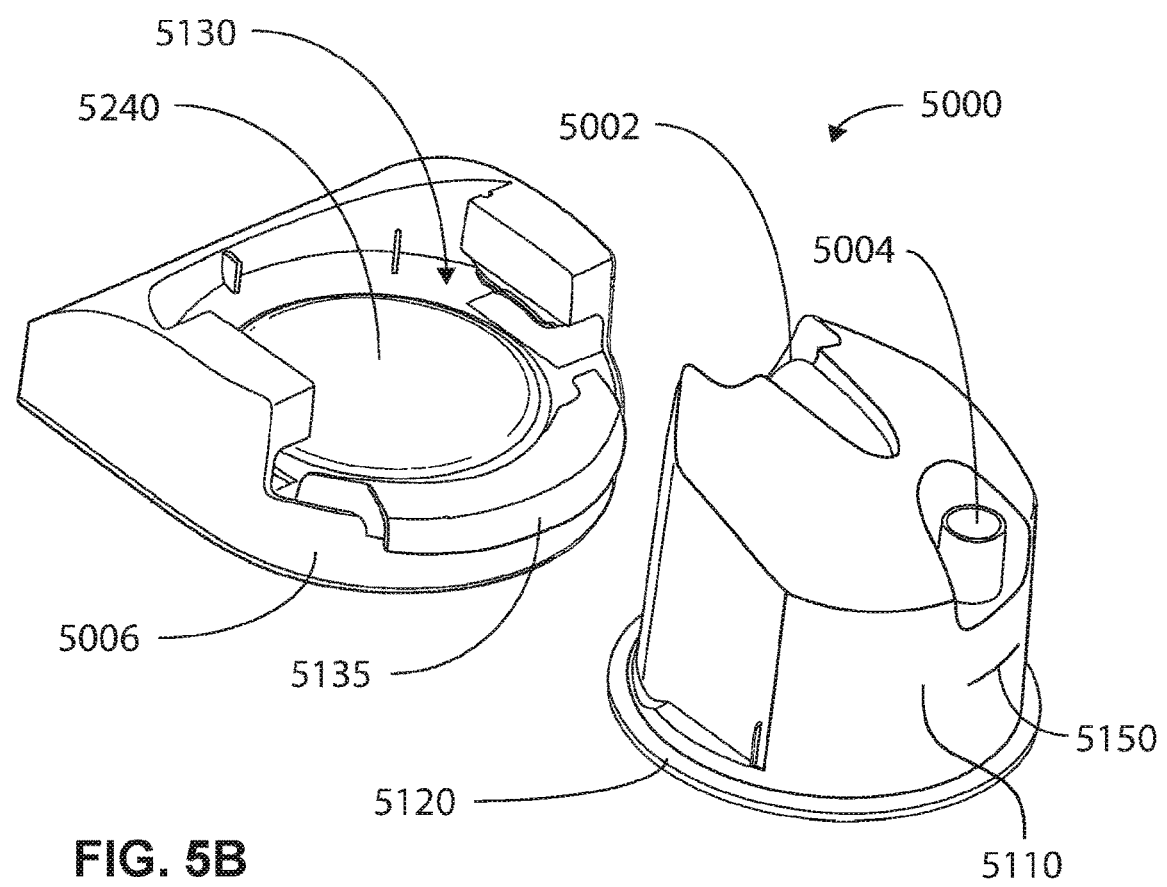

FIG. 5B shows an isometric view of an example humidifier in accordance with one form of the present technology, showing a humidifier reservoir 5110 removed from the humidifier reservoir dock 5130.

4.6 Breathing Waveforms

Figure 6:
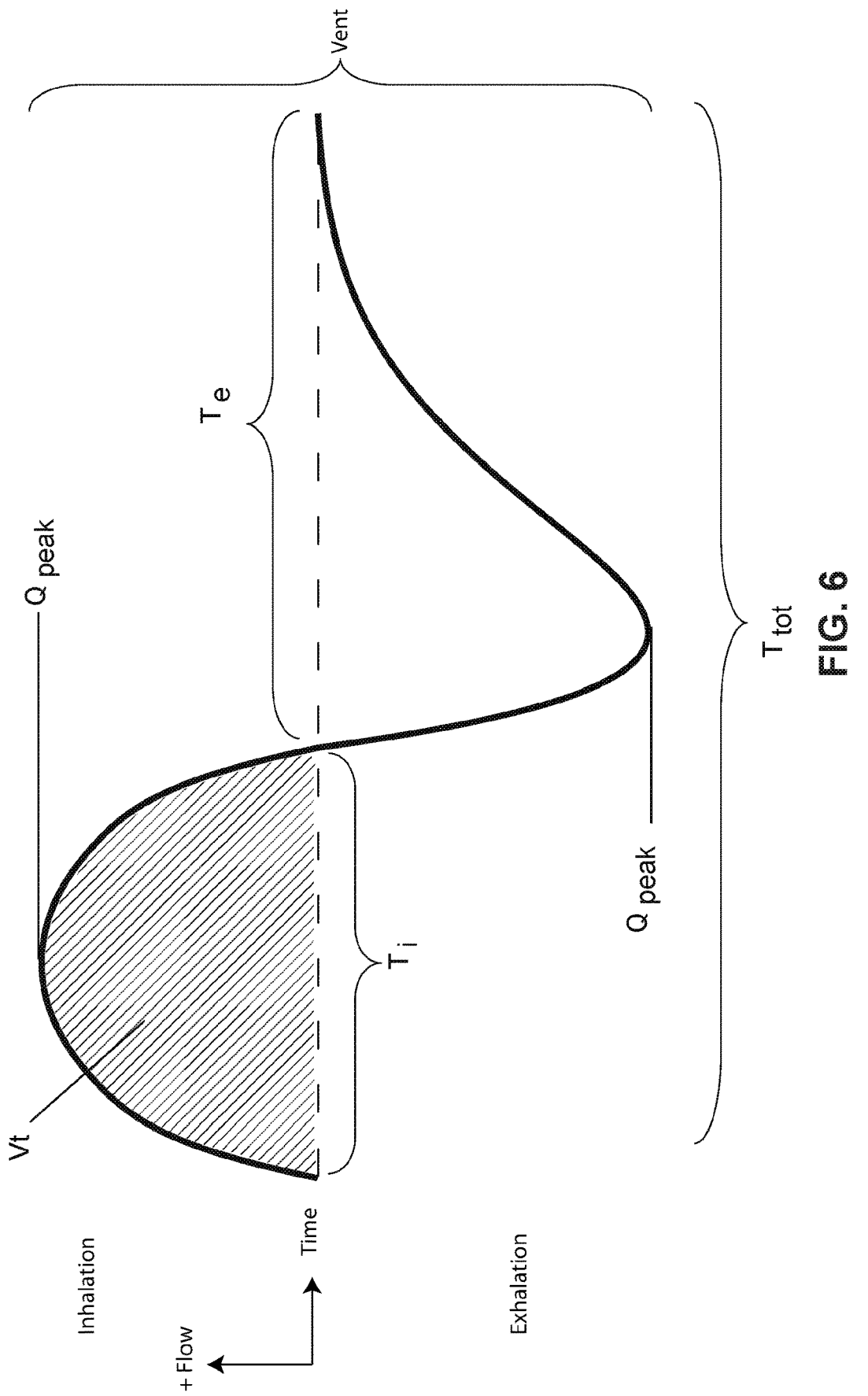

FIG. 6 shows a model typical breath waveform of a person while sleeping.

4.7 Status Determination

Figure 1:
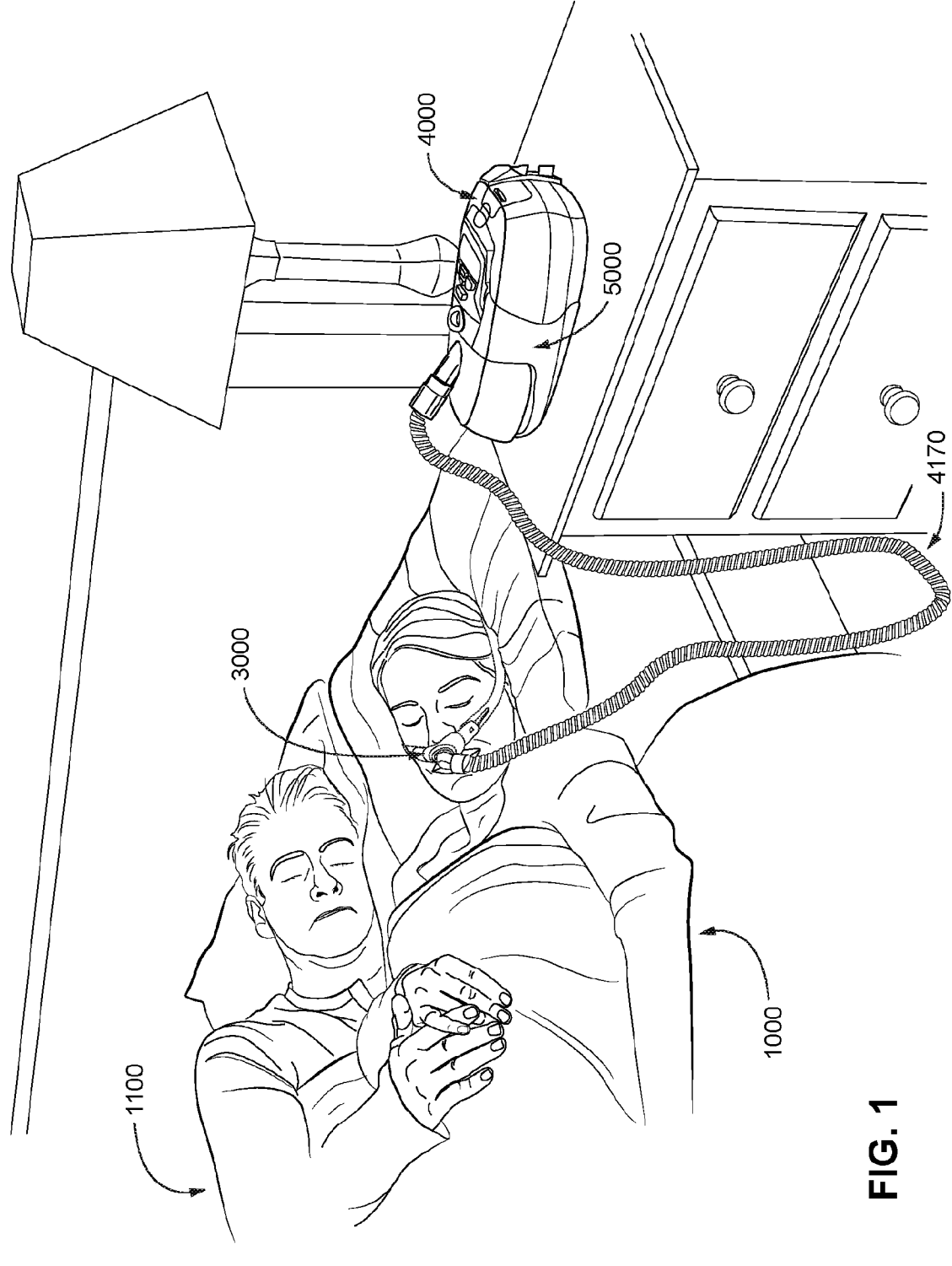
Figure 2:
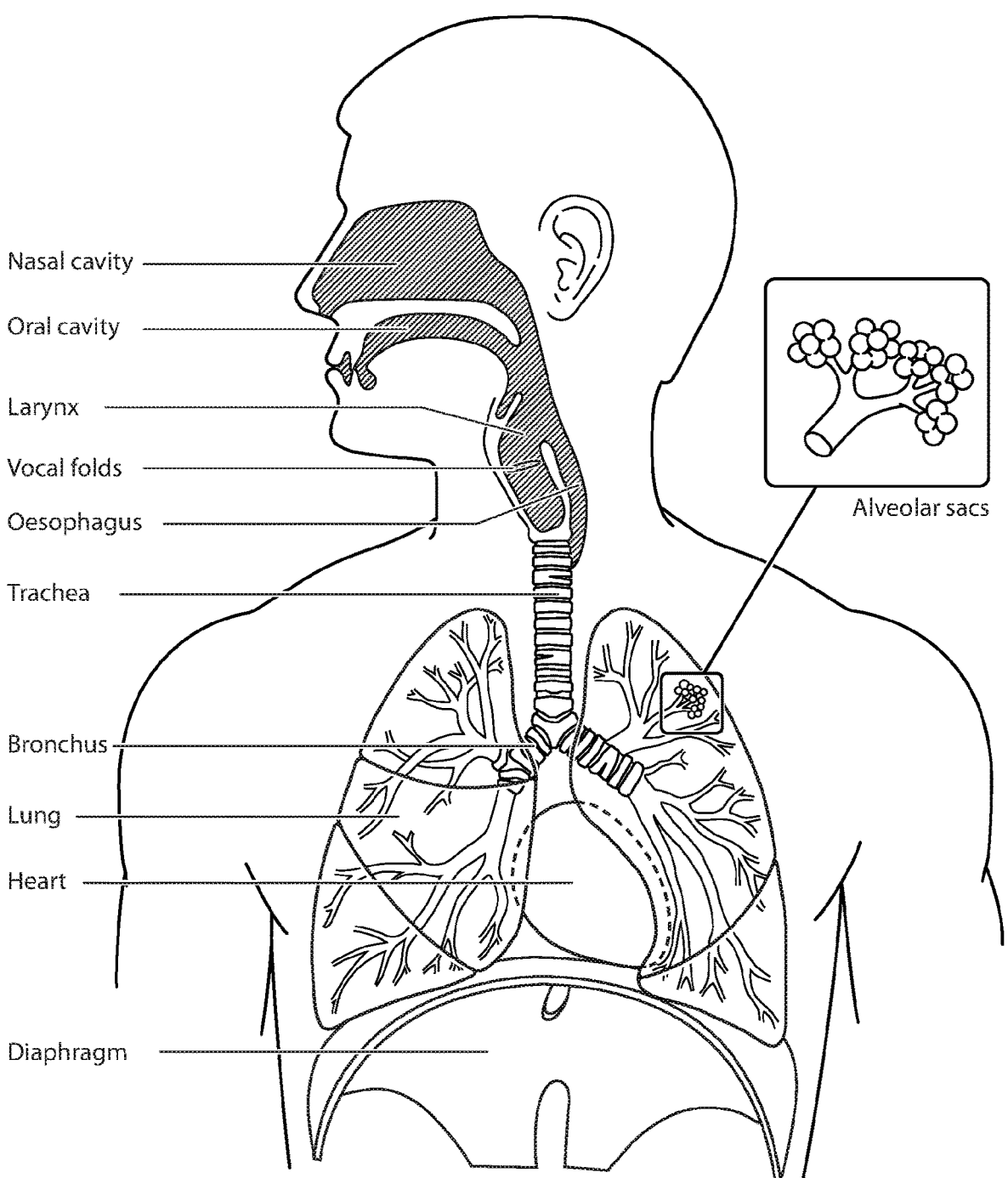
Figure 3:
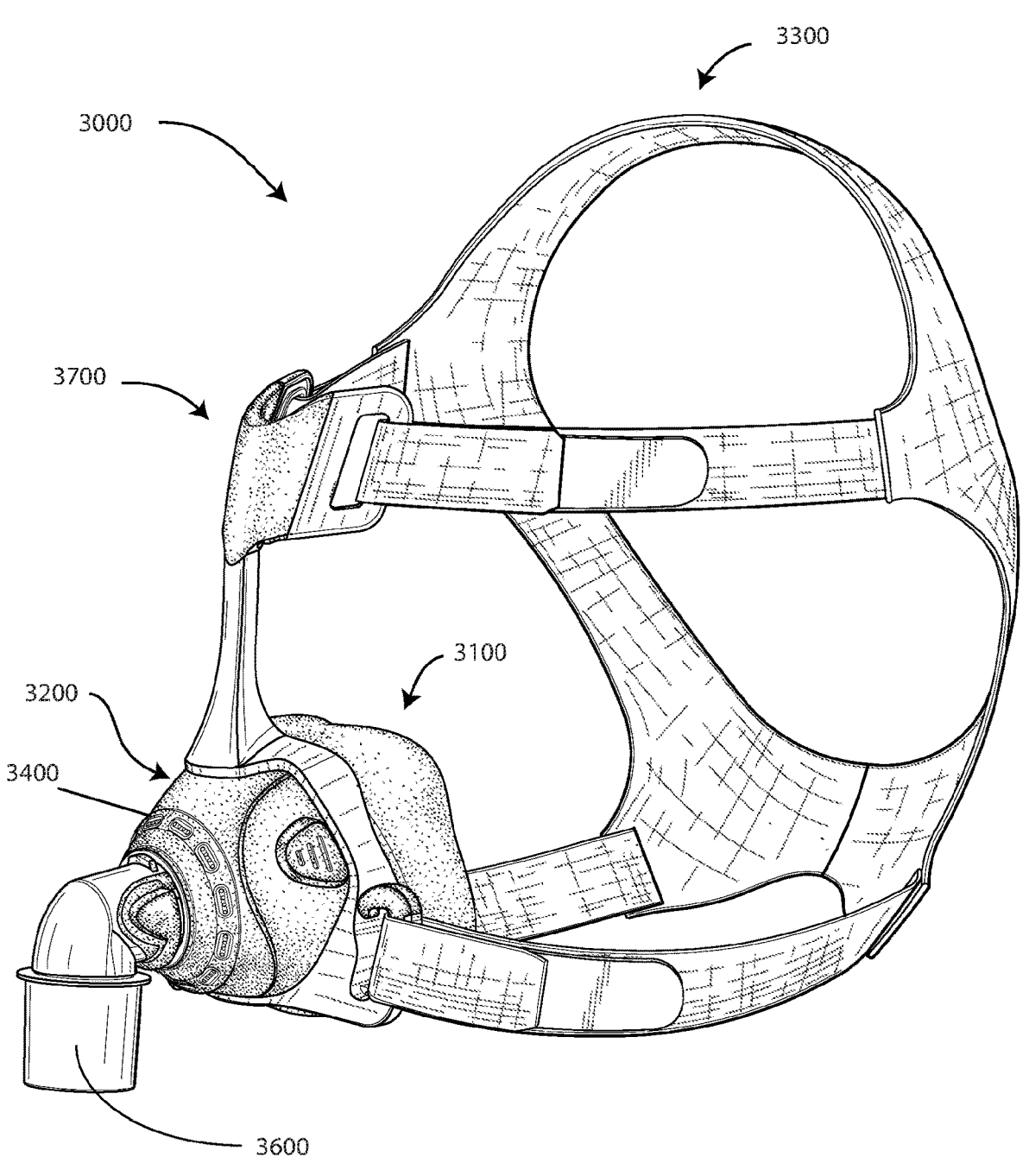
Figure 4A:
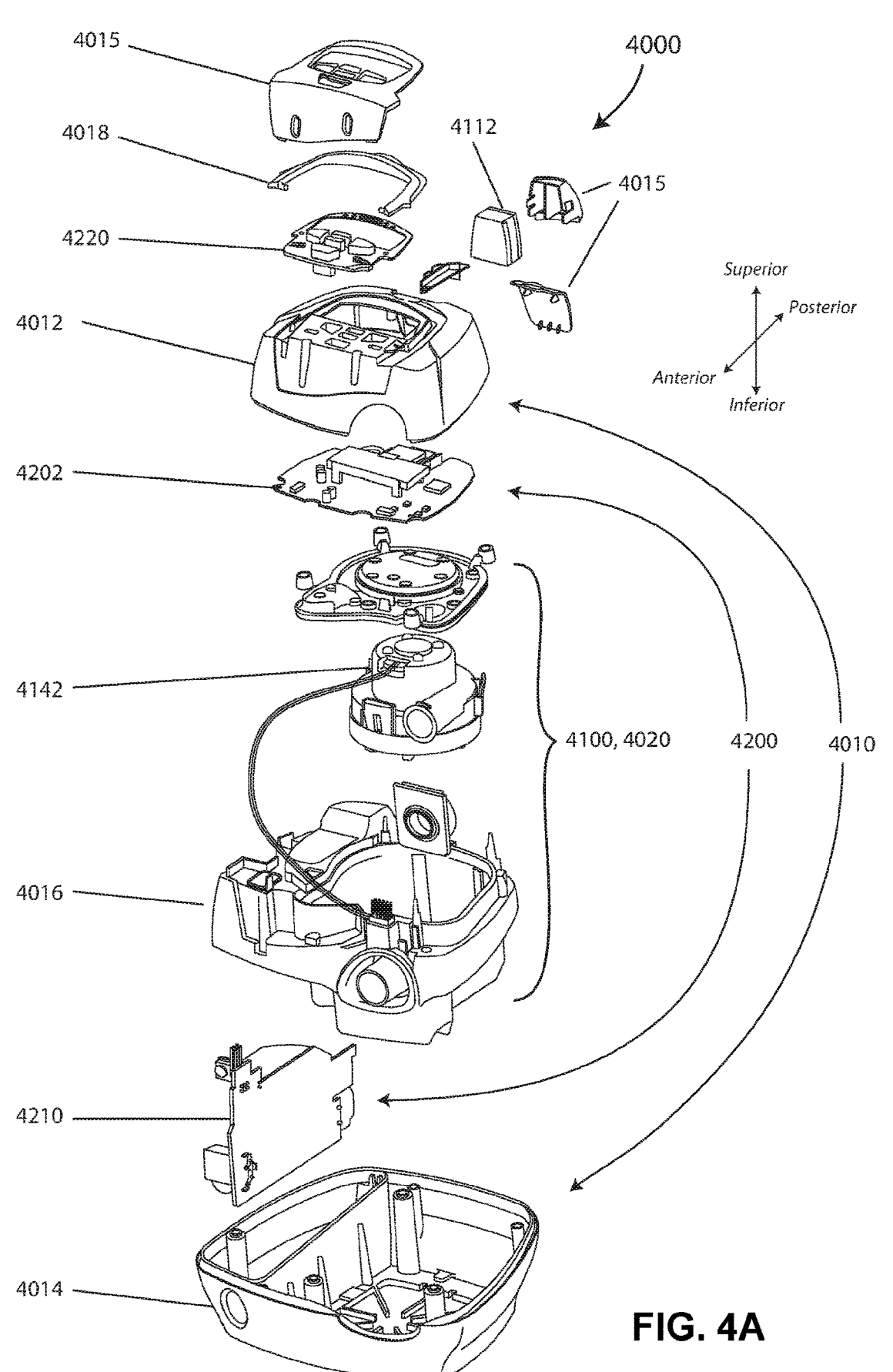
FIG. 4C is a schematic diagram of example electrical components of an RT device in accordance with one form of the present technology.
FIG. 4D is a schematic diagram of example algorithms implemented in an RT device in accordance with one form of the present technology.
Figure 4B:
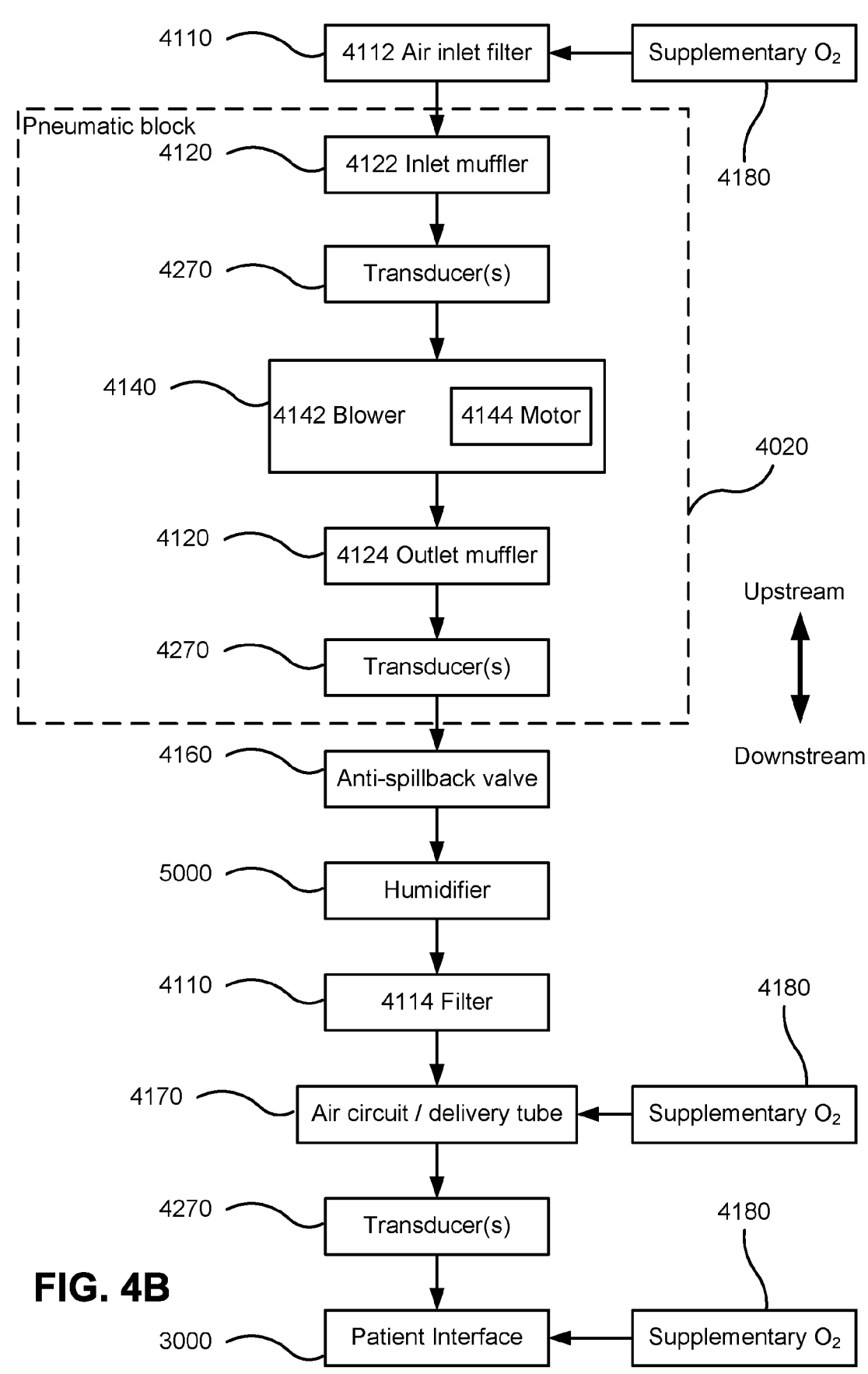
Figure 4C:
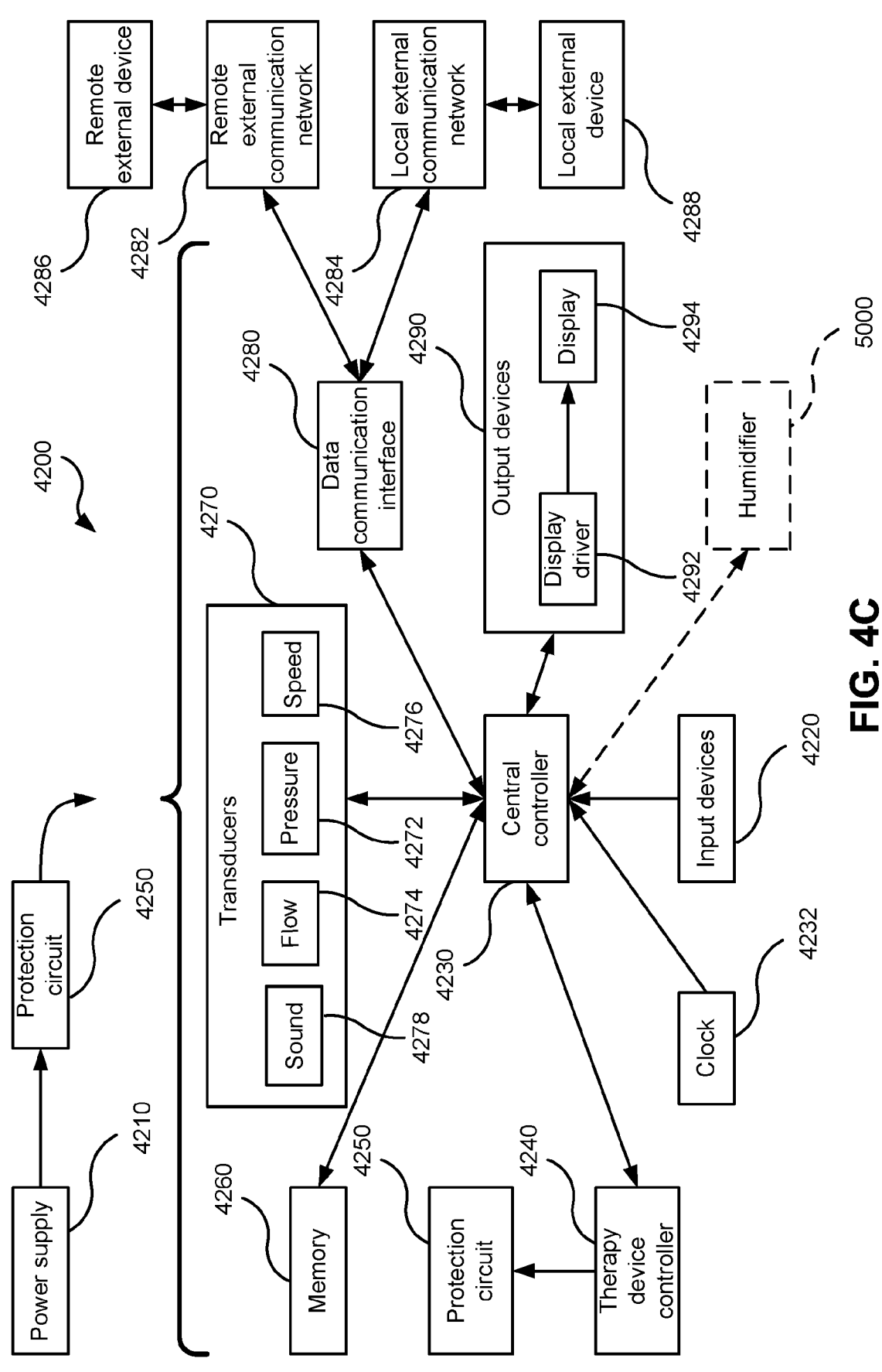
Figure 4D:
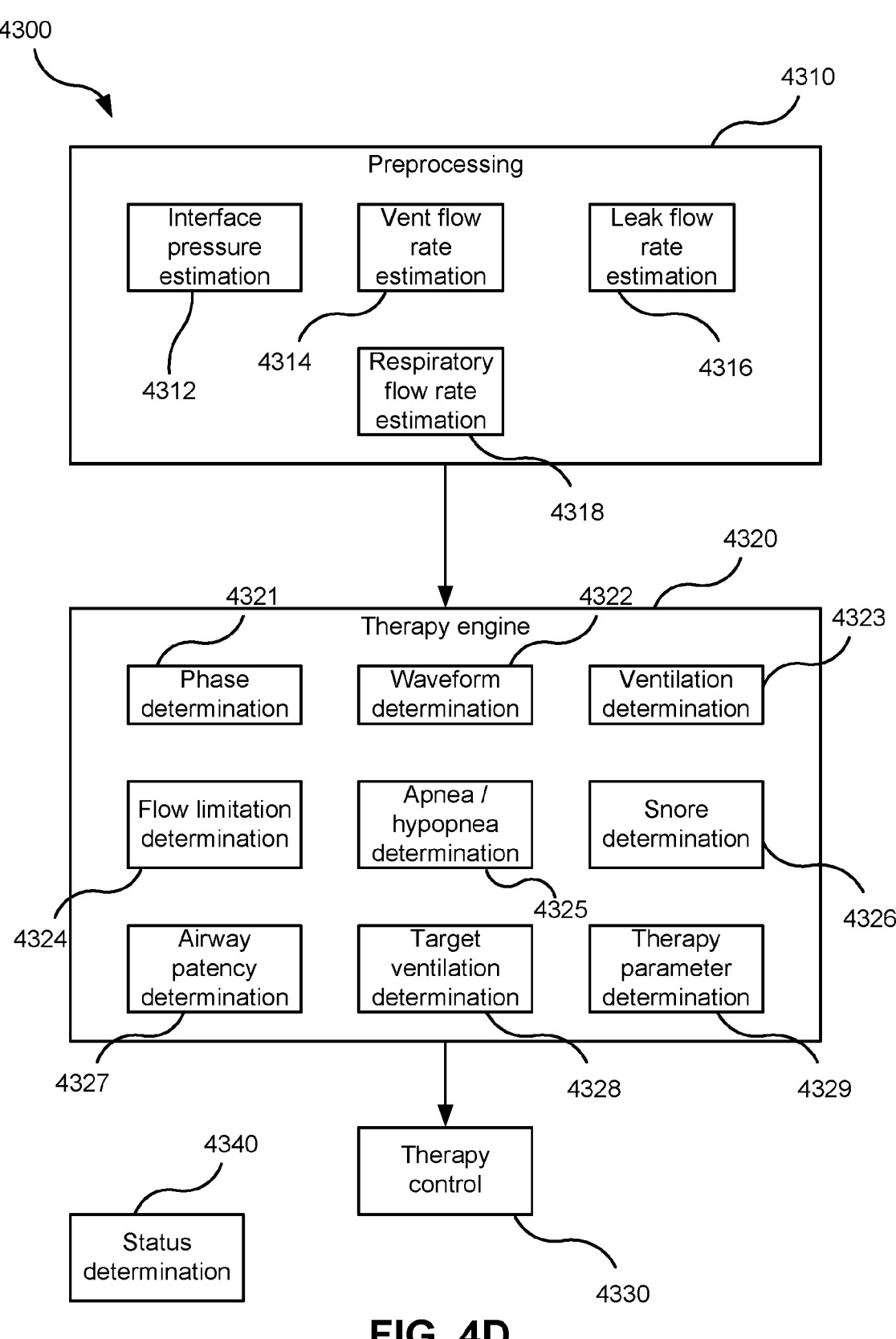
Figure 7A:
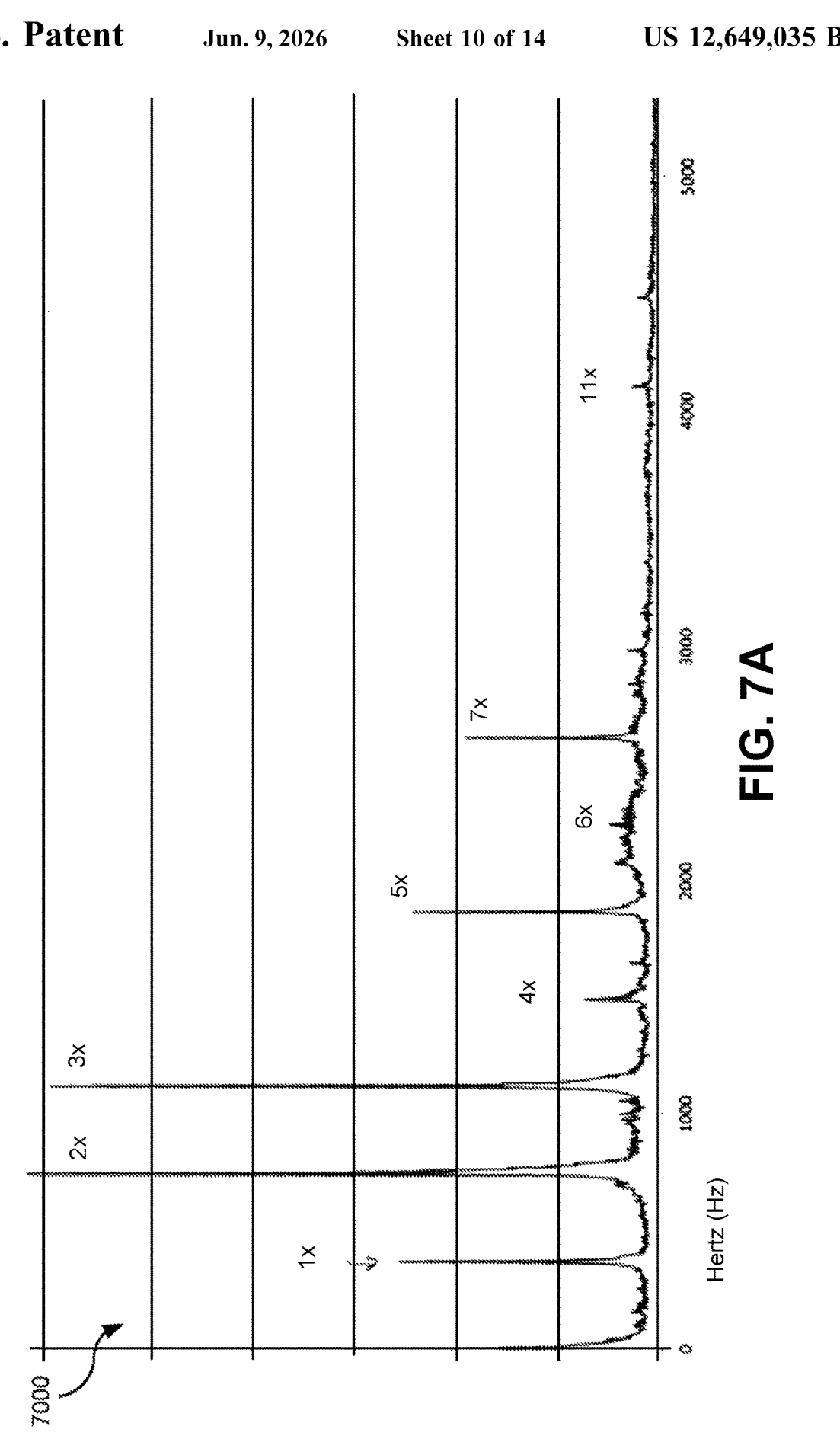
Figure 7B:
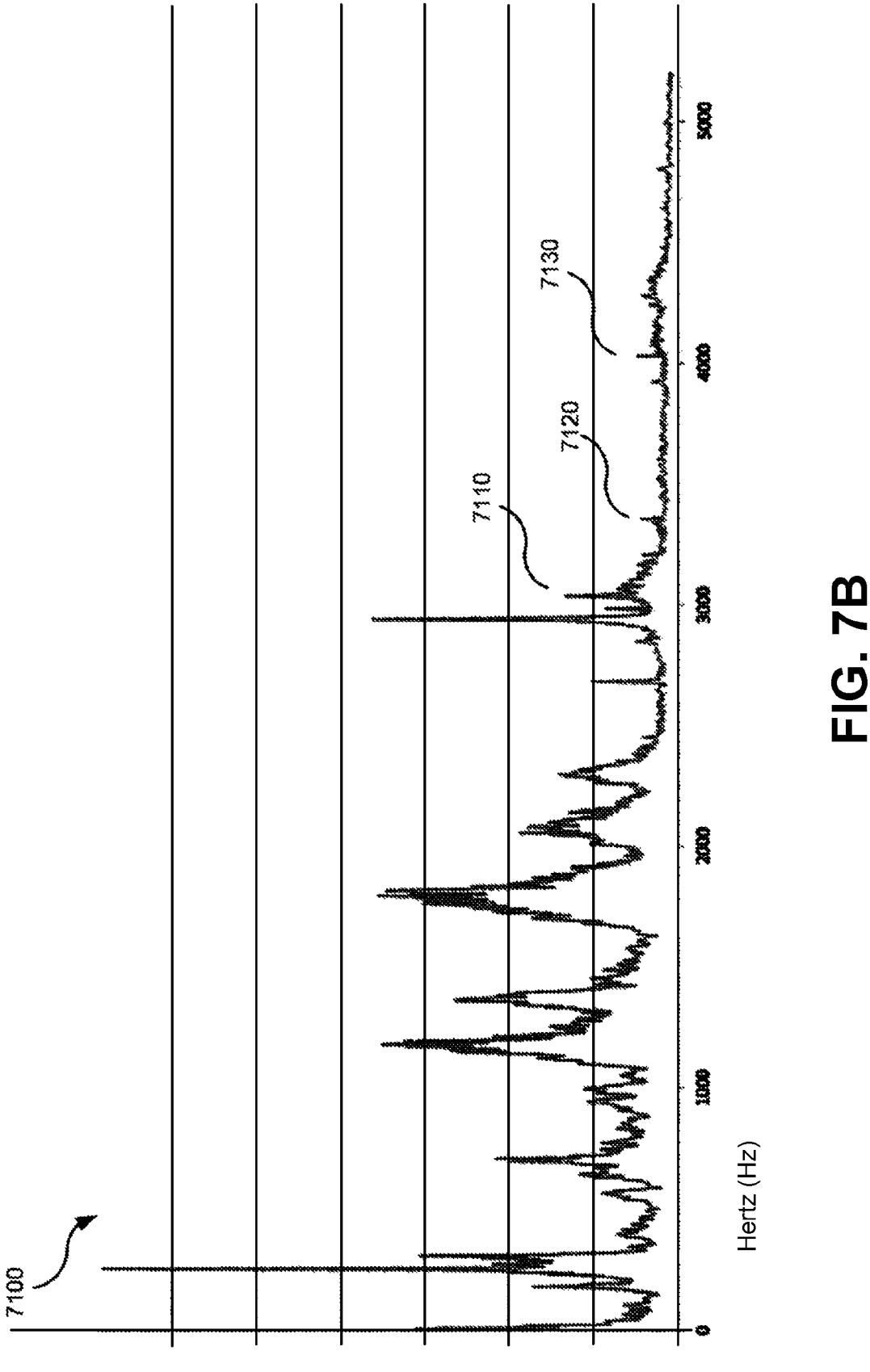
Figure 7C:
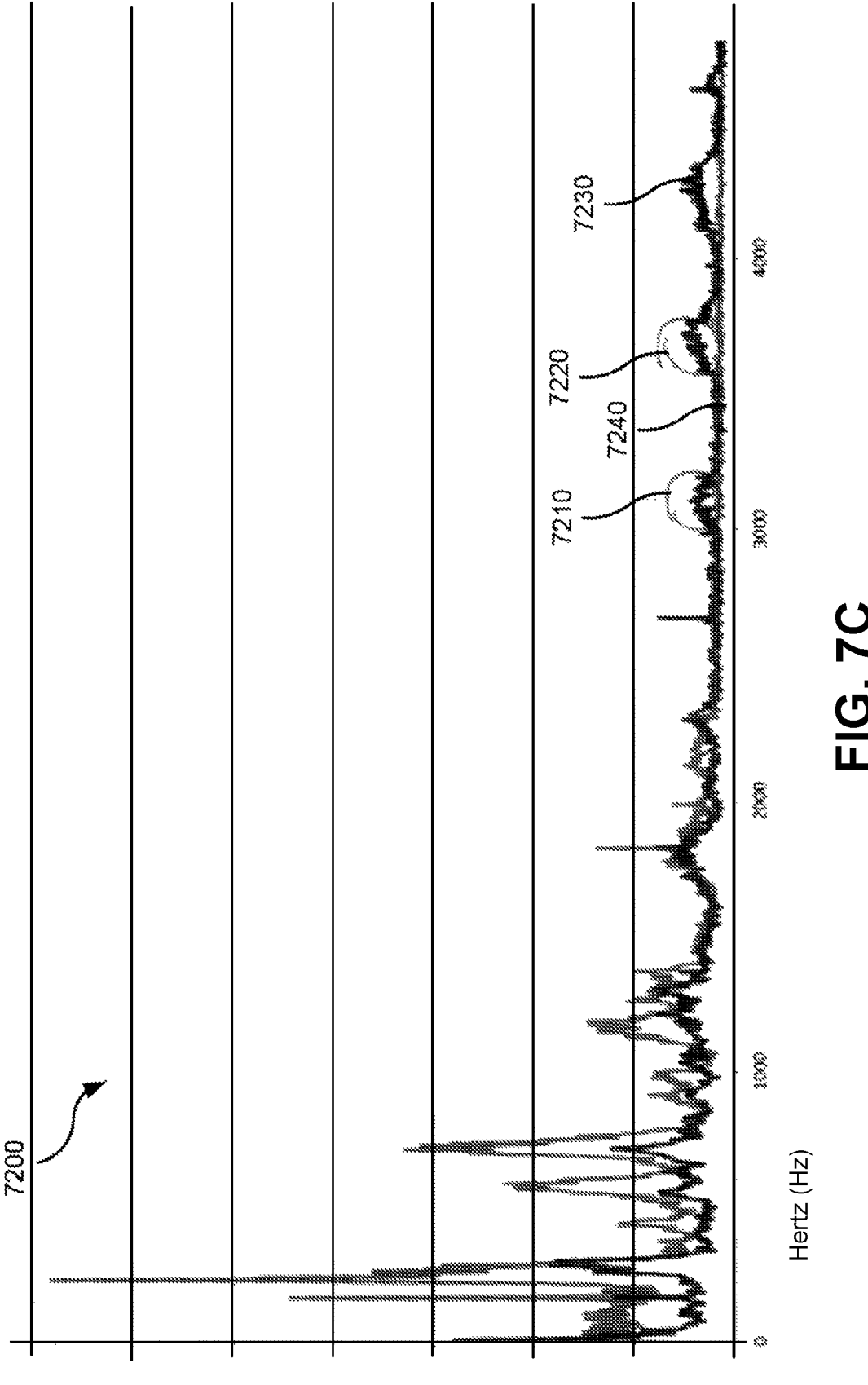

FIGS. 7A, 7B, and 7C contains example Fourier power density spectra of sound signals generated by a microphone in the air path of an RT device such as the device of FIG. 4A.

Figure 8:
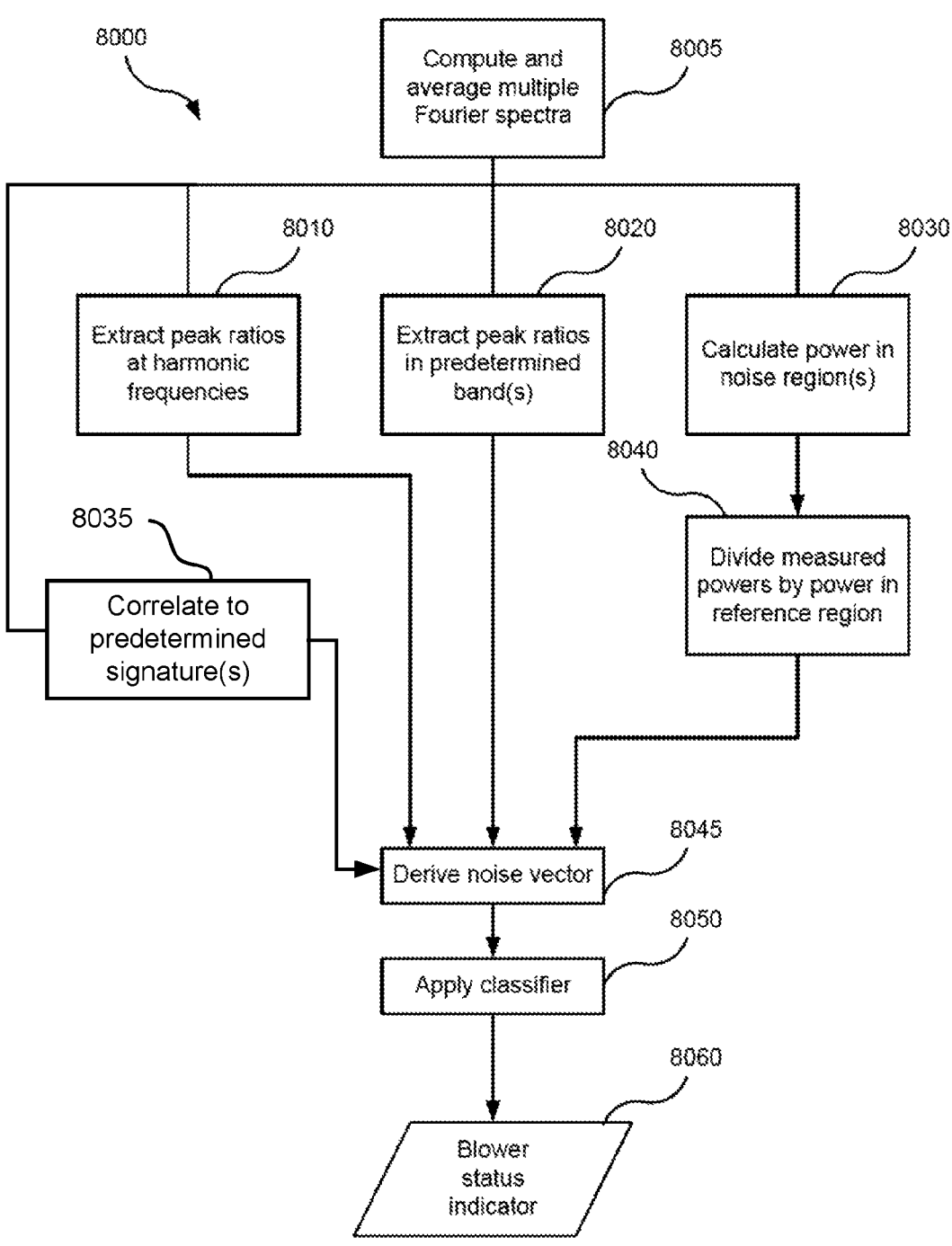

FIG. 8 contains a flow chart illustrating an example method of analysing sound signals generated by a sound transducer, such as a microphone, in the air path of an RT device such as the device of FIG. 4A so as to determine a status of the blower of the RT device.

Figure 9:
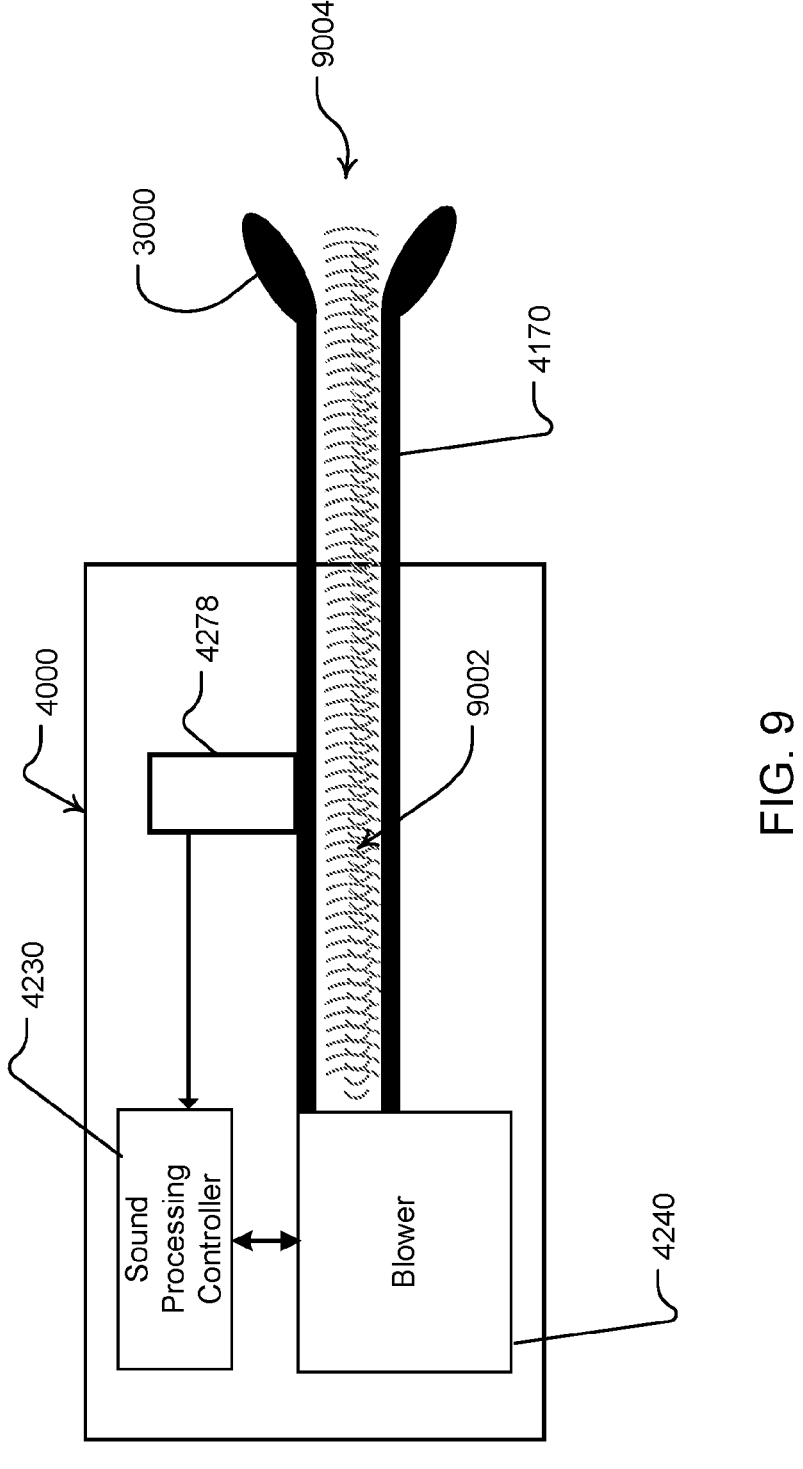

FIG. 9 is an illustration of an example status determination system showing a sound transducer 4278 for sensing the sound in an air path of the RT device 4000.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

5.4 Air Circuit

An air circuit 4170 in accordance with an aspect of the present technology is a conduit or a tube constructed and arranged to allow, in use, a flow of air to travel between two components such as RT device 4000 and the patient interface 3000.

5.5 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6 RT Device

An RT device 4000 in accordance with one aspect of the present technology comprises mechanical, pneumatic, and/or electrical components and is configured to execute one or more algorithms 4300, such as any of the methods, in whole or in part, described herein. The RT device 4000 may be configured to generate a flow of air for delivery to a patient's airways, such as to treat one or more of the respiratory conditions described elsewhere in the present document.

In one form, the RT device 4000 is constructed and arranged to be capable of delivering a flow of air in a range of −20 L/min to +150 L/min while maintaining a positive pressure of at least 6 cmH2O, or at least 10 cmH2O, or at least 20 cmH2O.

The RT device may have an external housing 4010, formed in two parts, an upper portion 4012 and a lower portion 4014. Furthermore, the external housing 4010 may include one or more panel(s) 4015. The RT device 4000 comprises a chassis 4016 that supports one or more internal components of the RT device 4000. The RT device 4000 may include a handle 4018.

The pneumatic path of the RT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RT device 4000 may include more than one PCBA 4202.

5.6.1 RT Device Mechanical & Pneumatic Components

An RT device may comprise one or more of the following components in an integral unit. In an alternative form, one or more of the following components may be located as respective separate units.

5.6.1.1 Air Filter(s)

An RT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.6.1.2 Muffler(s)

An RT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.6.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.6.1.4 Transducer(s)

Transducers may be internal of the RT device, or external of the RT device. External transducers may be located for example on or form part of the air circuit, e.g., the patient interface. External transducers may be in the form of non-contact sensors such as a Doppler radar movement sensor that transmit or transfer data to the RT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure, or a sound level at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.6.1.4.1 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 and representing a pressure is received by the central controller 4230.

5.6.1.4.2 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240 and/or the central controller 4230. The motor speed transducer 4276 may, for example, be a speed sensor, such as a Hall effect sensor.

5.6.1.4.3 Sound Transducer (Microphone)

In one form of the present technology a sound transducer (microphone) 4278 is used to generate a signal representing the sound generated in the air path by the blower 4142.

In one form, a signal generated by the microphone 4278 and representing the sound in the air path is received by the central controller 4230.

The microphone 4278 may, for example, be a specialised pressure sensor with a near-constant frequency response over the range from 10 Hz to 10 kHz. The microphone 4278 may be digital in the sense that the generated sound signal comprises a sequence of discrete data samples representing sound pressure values at a fixed sampling rate, e.g. 16 kHz. Alternatively, the microphone 4278 may generate a continuous-time (analog) sound signal. In the latter case, the controller 4230 may sample the sound signal from the microphone 4278 at a fixed sampling rate to generate the sequence of discrete data samples representing sound pressure values.

5.6.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.6.2 RT Device Electrical Components

5.6.2.1 Power Supply

A power supply 4210 may be located internal or external of the external housing 4010 of the RT device 4000.

In one form of the present technology, power supply 4210 provides electrical power to the RT device 4000 only. In another form of the present technology, power supply 4210 provides electrical power to both RT device 4000 and humidifier 5000.

5.6.2.2 Input Devices

In one form of the present technology, an RT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.6.2.3 Central Controller

In one form of the present technology, the central controller 4230 is one or a plurality of processors suitable to control an RT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 which may be implemented with processor-control instructions, expressed as computer programs stored in a non-transitory computer readable storage medium, such as memory 4260. In some forms of the present technology, the central controller 4230 may be integrated with an RT device 4000. However, in some forms of the present technology, some methodologies may be performed by an external device. For example, the external device may determine control settings for a ventilator or detect respiratory related events by analysis of stored data such as from any of the sensors described herein.

5.6.2.4 Clock

The RT device 4000 may include a clock 4232 that is connected to the central controller 4230.

5.6.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.6.2.6 Protection Circuits

The one or more protection circuits 4250 in accordance with the present technology may comprise an electrical protection circuit, a temperature and/or pressure safety circuit.

5.6.2.7 Memory

In accordance with one form of the present technology the RT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally, or alternatively, RT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.6.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.6.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.6.2.9.1 Display Driver

A display driver 4292 receives as an input the characters, symbols, or images intended for display on the display 4294, and converts them to commands that cause the display 4294 to display those characters, symbols, or images.

5.6.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.6.3 RT Device Algorithms

As mentioned above, in some forms of the present technology, the central controller 4230 may be configured to implement one or more algorithms 4300 with function(s) expressed as computer instructions or programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.6.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface pressure Pm, the vent flow rate Qv, the respiratory flow rate Qr, and the leak flow rate Ql.

In various forms of the present technology, the pre-processing module 4310 comprises one or more of the following algorithms: interface pressure estimation 4312, vent flow rate estimation 4314, leak flow rate estimation 4316, and respiratory flow rate estimation 4318.

5.6.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.6.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose interface pressure Pm at the patient interface 3000 is equal to the treatment pressure Pt. Additionally, or alternatively, the therapy parameter is a treatment flow Qt, and the therapy control module 4330 controls the pressure generator 4140 to deliver a flow of air whose interface flow or device flow Qd at the patient interface 3000 is equal to the treatment flow Qt.

5.6.3.4 Status Determination Module

In one form of the present technology, a module 4340 for the determination of a status of the RT device 4000 form part of the algorithms or modules 4300.

For example, the status determination module 4340 may include methods or processes for analysing, such as by signal processing, the sound signal generated by the microphone 4278 and representing the sound in the air path, such as the sound of operation of a motor of an RT device in the air path. The sound signal may be received by the central controller 4230. The analysis by a controller or processor may be applied to generate an output such as an indicator of the status of the blower 4142/pressure generator 4140 or one or more of its components. Examples of such signal processing may be considered in relation to the graphs of FIGS. 7A, 7B and 7C. Such signal processing may be based on a power density spectrum processing such as by Fourier transform (e.g., a fast Fourier transform (FFT) or discrete Fourier transform (DFT)). The processing may further involve peak detection and evaluation thereof, such as by computing peak ratios, and/or performing power evaluation.

FIG. 7A contains an example Fourier power density spectrum 7000 of a sound signal generated by a microphone in the air path of an RT device such as the device 4000. In the example, a motor, such as a motor that is a component of the pressure generator of the RT device, is controlled to operate at a motor speed of 22,500 revolutions per minute (RPM), which corresponds to a fundamental frequency of 375 Hz. If the Fourier power density spectrum contains significant peaks at integer multiples of the fundamental frequency, this may be an indication of an issue with the blower, or with a component of the blower. The spectrum 7000 shown in FIG. 7A does contain significant peaks at integer multiples of the fundamental frequency. In particular, the spectrum 7000 contains peaks at 375 Hz (the fundamental frequency), 750 Hz (twice the fundamental frequency), 1125 Hz (three times), 1500 Hz (four times), 1875 Hz (five times), and 2625 Hz (seven times). The heights of these peaks, such as in relation to the background noise, may be considered by a controller or processor as being potentially indicative of the status of the blower 4142. Such a potential indication may be derived by processing (by way of one or more computing operations) data associated with the spectral peaks at integer multiples of the fundamental frequency associated with the operation of the device motor. Accordingly, at least a part of the initial stage of data processing associated with obtaining the status indicator may be understood to be the application of a function to the data associated with these spectral peaks, namely an integer-multiple function. Thus, the integer-multiple function is configured for obtaining for evaluation the spectral peaks at one or more integer multiples of the fundamental frequency (e.g., motor fundamental frequency) from the spectrum rather than other peaks (e.g., non-integer multiple peaks) of the spectrum. For example, the specific peak distribution shown in FIG. 7A includes a number of relatively pronounced peaks at the lower integer multiples of the fundamental frequency that may be an indication of an issue with the motor drive shaft. A similar graph, but with the main frequency peaks being at the 1× and 11× integers (x being the fundamental frequency), may be an indication of a potential issue with the impeller (the 1× frequency corresponding to the impeller as a whole, and the 11× frequency corresponding to each of the 11 blades of the impeller). Such peaks may then be processed by the integer-multiple function such as to obtain peak ratios for further evaluation or classification.

FIG. 7B contains another example Fourier power density spectrum 7100 of a sound signal generated by a microphone in the air path of an RT device such as the device 4000. In this example, the motor, such as a motor that is a component of the pressure generator of the RT device, is controlled to operate at a motor speed of 15,000 RPM, which corresponds to a fundamental frequency of 250 Hz. The spectrum 7100 contains significant peaks at non-integer multiples of the fundamental frequency. Such non-integer multiples of the fundamental frequency may be an indication of an issue with one or more ball bearings. For example, the peak 7110 is at 3039 Hz, i.e. 12.15 times the fundamental frequency of 250 Hz, while peak 7120 is at 3355 Hz, i.e. 13.42 times the fundamental frequency, and peak 7130 is at 4027 Hz, i.e. 16.1 times the fundamental frequency. The heights of these peaks, such as relative to the background noise, may be considered by a controller or processor as being indicative of the status of the blower 4142. In particular, the relative heights of these non-integer multiple peaks may be considered to be indicative of the status of the motor 4144, and in particular, the bearings of the motor 4144. Such a potential indication may be derived by processing (by way of one or more computing operations) data associated with the spectral peaks at non-integer multiples of the fundamental frequency associated with the operation of the device motor. Accordingly, at least a part of the initial stage of data processing associated with obtaining the status indicator may be understood to be the application of a function to the data associated with these spectral peaks, namely a non-integer-multiple function. Thus, the non-integer-multiple function may be configured for obtaining for evaluation the spectral peaks at one or more non-integer multiples of the fundamental frequency (e.g., motor fundamental frequency) from the spectrum and may omit other peaks (e.g., integer multiple peaks) of the spectrum. Such peaks may then be processed by the non-integer-multiple function such as to obtain peak ratios for further evaluation or classification.

FIG. 7C contains another example Fourier power density spectrum 7200 of a sound signal generated by a microphone in the air path of an RT device such as the device 4000. In this example, the motor, such as a motor that is a component of the pressure generator of the RT device, is controlled to operate at a motor speed of approximately 12,000 RPM. The spectrum 7200 contains three "bulges" 7210, 7220, and 7230 that are above background power in respective "resonant regions" between 3000 Hz and 5000 Hz. The resonant regions represent either structural resonances or air cavity resonances that are within the blower 4142 or within the RT device 4000 and may be considered by a controller or processor as being indicative of the status of the blower 4142. For example, the amount of power in each resonant region, divided by the power in a reference region that is otherwise known to be "quiet" (low in power) regardless of blower status, may be considered by a controller or processor as being indicative of the status of at least a component (e.g. one or more ball bearings) of the blower 4142. What region may be nominated as quiet may depend on the specific device and configuration. Some considerations may include that a "quiet" region exhibits a/a noise level that is a predetermined percentage of the values of the adjacent peaks, or b/that the region exhibits similar noise values regardless of whether there is a blower fault or not. One example of such a reference region is labelled as 7240 in the spectrum 7200. The obtained ratio may then be compared with a predetermined threshold, such as by a classifier described herein, the value of which will depend to a large extent on the specific type and configuration of the device used in the test. Since such an indication corresponds to one or more resonant frequencies, such an indicator may be understood to be the result of application of a function, namely a resonant frequency function, of a resonant frequency attributable to operation (RPM) of the motor.

The motor speed at which the frequency response is evaluated, can either be built-in and selectable (e.g., a setting of the controller of the motor) within the respiratory therapy device, or can be remotely dialled in and set remotely for a periodic or on-demand evaluation, such as by communication to the controller of the motor from an external computer, such as an external computer over a network.

Generally, different faults of different components of the blower can best manifest themselves at different speeds that may depend on the specific element and on the mechanical configuration of the blower. However, almost all blower faults are better manifested at higher motor speeds. Whilst a higher speed is thus usually preferred for better presentation of most faults, various commercial, mechanical and software limitations can also affect the choice of the speed used for obtaining the graphs shown in FIGS. 7A to 7C. For example, very high speeds may be associated with a higher level of noise which may bother the user. In addition, the highest speeds may trigger various protection mechanisms (i.e., one such mechanism is the "stall detection" which looks at motor current vs pressure and may turn off the device if a combination of high current and low pressure is detected). Thus, from marketing perspective and from the perspective of user comfort, the highest available speeds for a given device may not be the most desirable. Thus, for deriving/generating the data (e.g., data of graphs of FIGS. 7A to 7C) used for detecting various faults, it is generally recommended to run the motor at maximum practical speed, determined by any mechanical, software, operational and commercial considerations applicable to the specific device, the specific use and potentially—the specific user. Nevertheless, many faults may manifest themselves within a relatively wide range of speeds. For example, whilst the data for graphs of FIGS. 7A to 7C are generated at three different motor speeds, similar data may be generated at each one of these speeds.

A quick scan that operates the motor through a number of speeds of a given device with a particular fault can also be used to indicate the most suitable range of speeds for deriving data for such graphs. In addition, whilst the data of the graphs in FIG. 7A-C have been associated with potential issues of the blower, this association is likely to be relevant to the specific device design and configuration (e.g., ResMed's AirSense 11 CPAP device). Whilst the equivalent data or graphs of devices of different designs may be generally similar, at least some differences in the data of the graphs can be expected. Thus, one practical approach for any type/design of RT devices, would be to test a number of devices preferably having different faults, at a number of motor speed ranges. Such a test may serve to determine a link between each of these faults and unique frequency/spectrum data such that a frequency or frequency region can serve as a "signature(s)" that may be associated with the particular fault. Such a signature may be data similar to that shown in FIGS. 7A-7C. Once identified (e.g., stored in a system or RT device), these "signature(s)" can then be used to indicate a potential fault in further devices of the same design, such as when test data from a similar test/diagnostic process of any of the further devices is compared to the signature(s), such as by a statistical correlation function that serves as a process to compare spectrum data of the signatures, such as to produce a score of similarity between the test spectrum data and the signature(s). The ability to identify potential faults with the blower and potentially being able to identify specific components with which the fault may be associated, can be very useful for remote diagnostic and maintenance of the devices, as well as for ensuring a continuous and non-interrupted treatment to the patient. FIG. 8 is a flow chart illustrating a method 8000 of determining the status of a blower in an RT device, e.g. the RT device 4000, by analysis of the sound signal generated by a sound sensor, such as a sound transducer or the microphone 4278, such as where the generated sound signal represents the sound in an air path of the RT device, such as the sound of operation of a motor of an RT device in the air path. An example of a sound transducer 4278 for sensing the sound 9002 in the air path 9004 of the RT device 4000 is also illustrated in FIG. 9. Whilst FIG. 9 shows the transducer 4279 being located somewhere along the length of air circuit 4170, other variations may be implemented. For example, the transducer 4278 may be located anywhere along the air path—such as from an air inlet of the RT device to the patient interface 3000. Furthermore, the transducer may even be located outside the air path and anywhere in, or on, the device, such as in the vicinity of, on the housing of, or even inside, the blower 4240. When out of the air path, the transducer may still be in a fluid communication with the air path and, therefore, with the sound waves propagating along the air path (i.e., see PCT/AU2021/050340 filed 16 Apr. 2021). However, this does not have to be the case and the transducer may be both out of, and out of fluid communication with, the air path.

The method may be carried out in whole or in part by one or more controllers or processors, such as by executing programming instructions of a processor or controller in the RT device and/or a processor or controller in communication with the RT device. The method 8000 may be carried out during a "diagnostic period" in which the motor 4144 is set to operate at a predetermined speed, with no patient connected to the patient interface 3000. The predetermined motor speed in RPM divided by 60 sets the fundamental frequency of the analysis (in Hz). A diagnostic period may be appended to each therapy session. For example, the diagnostic period may be operated before and/or after a patient therapy session with the RT device and the aforementioned signal processing may be applied to the sensor signal data sensed from the diagnostic period. Moreover, the method may apply any one or more of the aforementioned functions. For example, it is recommended to consider the data associated with all of FIGS. 7A to 7C, or at least the combination of FIGS. 7A and 7B. However, each of FIGS. 7A to 7C (each associated with a respective path in FIG. 8) can provide an indication of a potential fault with the blower and may thus potentially be used on its own.

A potential benefit of conducting the above diagnostic/test methodologies when normal therapy mode of the device is not operating, is that the motor may be then be run or controlled by the controller in a speed mode. In contrast, during standard operation of such devices in a therapy mode, the motor may typically be run under the control of controller in a pressure control mode or flow control mode. In such modes, constantly changing pressure or flow may correspond to a constantly changing speed of the motor, potentially resulting in undesirable continuous change in the recorded data for the spectra related functions/evaluation. Also as otherwise explained herein, the above methodologies may be conducted at relatively high motor speeds, not usually associated with some therapy modes such as a pressure control mode of a standard pressure therapy session.

Nevertheless, conducting the above blower diagnostic methodologies during a therapy mode may be implemented. One example implementation for such testing may be to coordinate the test at suitable time during therapy, such as in response to a type of detected respiratory event. For example, the test may be conducted (i.e., sound recorded for evaluation by the aforementioned function concerning spectra data), during a apnoea event type, which may coincide with a period of time when the motor speed is relatively constant. Similarly, one may also perform the sound measurement by gating the sound recordings in relation to a number of breaths. For example, the sound measurement may be parsed to obtain data from similar sub-portions of each breath from multiple breaths. This may be done, for example, by taking the data from a small time interval (e.g., a time period of less than a single breath, such as from about 0.1 s to about 0.5 s) for each of a number of breaths that are consecutive and/or not consecutive. The chosen interval may be one that coincides with blower motor operation at a relatively or approximately constant speed, such as at a predetermined speed (e.g., a predetermined speed range) and/or at a certain time within each breath cycle as monitored by a breathing cycle detection or phase determination process otherwise described herein. For example, the interval may be taken from each end expiratory pause or a period preceding beginning of each inspiration of a plurality of breaths. The sound data from the intervals may then be combined into the sound signal for obtaining data (e.g., frequency/spectra) as previously described in relation to the example data shown in any of FIGS. 7A-7C. Optionally, such a process may be performed so as to satisfy a minimum quantity to ensure that a sufficient number of intervals are obtained for determining the spectrum. For example, the intervals may be collected until the number of breaths associated with combined intervals satisfies at least a predetermined number of breaths, such as between about 50 and 100 breaths or other number depending on actual interval length to ensure collection of enough data for the analysis at the approximately constant speed. Additionally, the intervals may be collected until the total time associated with combined intervals (e.g., the accumulated time of all of the intervals) at least satisfies a predetermined total time amount, such as about at least 10 minutes of recorded sound, for example.

For example, the method 8000 may start at step 8005, which involves the processor or controller receiving a sound signal generated by the sound transducer for generating one or more frequency spectrums such as Fourier spectra. The sound signal may be segmented into windows or portions of the sound signal. Thus, the processor or controller may capture the signal and segment the data of the sound signal into one or more windows of the sound signal, such as in a manner previously described with regard to the parsed intervals. In one implementation, step 8005 captures ten windows. Each window may comprise a predetermined number of samples of the sound signal, e.g. 4096 samples. At step 8005, the processor or controller may also apply signal processing to the input sound data such as the windows. For example, a Fourier transform may be applied to the data or each window to compute a Fourier spectrum of the data or window. The frequency resolution of the Fourier spectrum is the sampling frequency divided by the number of samples in the window. For example, if the sampling frequency is 16 kHz and the number of samples in each window is 4096, the frequency resolution of the Fourier spectrum is 3.9 Hz (234 RPM). In some implementations, the predetermined motor speed in RPM is an integer multiple of the frequency resolution, in units of RPM. In the example in which the sampling frequency is 16 kHz and the number of samples in each window is 4096, motor speeds of 11250 RPM and 13125 RPM are integer multiples of the frequency resolution. Step 8005 may then combine a plurality of Fourier spectra into a single combined Fourier spectrum, e.g. by averaging or other combining operation, such as if combining is performed.

The method 8000 may proceed to any one or more of the functions of steps 8010, 8020, 8030 and 8035. Optional steps 8010, 8020, 8030, and 8035 may each operate on an input Fourier spectrum, such as the combined Fourier spectrum, and may take place in parallel or in any order. Step 8040 may follow step 8030.

Step 8010 extracts one or more peaks at integer multiples of the fundamental frequency (harmonic frequencies), up to some predetermined maximum multiple (e.g., 12) such as by applying an integer multiple function. Such a function locates peaks, and derives assessment data values with the associated peaks, such as peak ratios, where the peaks are located at or near integer multiples of the fundamental frequency attributable to operation (RPM) of the motor. For example, step 8010 may divide each peak height by the root-mean-square (RMS) power in a band surrounding the peak, e.g., a band of width 40 Hz, or a band of width 80 Hz that includes each side band at a width of 40 Hz to determine a data set of values of the harmonic peak ratios that are attributable to the one or more peaks at integer multiples of the fundamental frequency. The use of ratios aims to take into account and mitigate the effect of any background noise in the respective frequency range. The resulting assessment data values may be considered/classified by a classifier, such as a classifier as described in more detail herein.

Step 8020 extracts one or more peaks at non-integer multiples of the fundamental frequency within a predetermined region, such as by applying a non-integer multiple function. In one implementation, the predetermined region may be 2 kHz to 4 kHz or 1.5 to 4 kHz. The predetermined region may be selected based on the type of the motor 4144. The non-integer-multiple function locates peaks, and derives assessment data values with the associated peaks, such as peak ratios, where the peaks are located at non-integer multiples of the fundamental frequency attributable to operation (RPM) of the motor. Such assessment data values may be considered/classified by a classifier, such as a classifier as described in more detail herein. For example, step 8020 may divide the height of each extracted peak by the RMS power in a band surrounding the peak to determine a data set of values of the non-harmonic peak ratio(s) that are attributable to the one or more peaks at non-integer multiples of the fundamental frequency. As in the case with the integer multiplies in FIG. 7A, some of the peaks in FIG. 7B may be background related and exist in the scan of a device with no particular fault. However, the use of peak ratios may mitigate this by reducing the effect of the background on the height of the peak. In one implementation, the peaks are searched for in predetermined intervals (e.g., 80 Hz), and the surrounding band for each peak may be a predetermined range or band width (e.g., 40 Hz). In some cases, i.e., when both steps 8010 and 8020 are effected, if a peak is found at a harmonic frequency, such a peak may be discarded as it can be otherwise analysed at step 8010. In some implementations, both the harmonic and non-harmonic peak ratios may be evaluated by comparison with one or more threshold (s) such as one or more predetermined threshold(s) (e.g., a threshold or a predetermined threshold). For example, both harmonic and non-harmonic peak ratios below a predetermined ratio threshold (for example 1.9 for both harmonic and non-harmonic) may be omitted from the data set. The threshold may be different from the above number and may vary, in this specific type of device (ResMed's AirSense 11), between, for example, 1.8 to about 5. The predetermined ratio threshold may be received by the process of method 8000 from an external computing device such as the remote external device 4286 or the local external device 4288.

Optionally, a certain number of highest peak-to-base ratios may be sent to the external computing device and/or remote external device or other remote system, without any threshold (e.g., by sending a highest set of the ratios [e.g., five highest ratios].) Then the recipient remote and/or external devices/system can determine the threshold.

In some implementations, the data set may be limited to a maximum number of non-harmonic peak ratios, e.g., five (5). In one example, the five largest ratios may be chosen. Each non-harmonic peak ratio in the data set may be paired with data representing the non-integer multiple of the fundamental frequency at which the corresponding non-harmonic peak was located.

In the above text, several functions (e.g., steps 8010 and 8020) were discussed in relation to locating peaks and deriving assessment data values that are associated with the peaks. As previously described, an example derived value of any of these functions may be a calculated peak ratio. However, alternative and/or additional values may be derived by any of these functions. For example, instead of or in addition to deriving a ratio, the applied function may derive a peak related value by subtracting a value of the background power (such as power at a predetermined frequency range in the base of the peak), from the peak value. Alternatively, or additionally, the applied function may derive a peak related value by subtracting from the peak, a value of one or more other peak(s) at a specific frequency (ies) relative to the peak (such as by subtracting from the peak an averaged value of adjacent peaks (e.g., peaks of the two frequencies on each side) or a predetermined frequency range away from, the peak). Step 8030 calculates the average power within one or more predetermined "resonant regions" of the Fourier spectrum, such as by applying the resonant frequency function. Such a function locates resonant regions, and derives assessment data values with the associated regions, such as power data, that contain a resonant frequency attributable to operation (RPM) of the motor. Each resonant region may span a range of frequencies, such as approximately 200 hertz, 450 hertz or other. In one implementation, there are three resonant regions: 3000 to 3200 Hz, 3550 to 3900 Hz, and 4200 to 4400 Hz. The assessment data values may be considered/classified by a classifier, such as a classifier as described in more detail herein. An optional step 8040 may include dividing the average power within each resonant region by the RMS power of a "reference region" that is known or predetermined to be quiet regardless of blower status, to obtain a data set of values that may be considered "noise ratios." In one implementation, the reference region is 3300 to 3500 Hz. The frequencies of the reference region may be non-overlapping with the frequencies of the resonant region(s).

As previously mentioned, step 8045 may process the spectra data in relation to one or more pre-captured (e.g., previously stored) spectra signature(s), such as by one or more statistical correlation functions, so as to determine a similarity between the spectra and the signature(s). Typically, such signature(s) will be spectra derived from sound recording of blowers with particular diagnostic problems/ fault(s). Thus, the step 8045 may produce one or more scores of similarity/correlation between the test spectrum data and the fault related signature(s), which may be further evaluated such as by inclusion in the vector of 8045 for classification, such as by a classifier at 8050 as discussed in more detail herein.

In this regard, one can detect if the blower is noisy or exhibiting a particular noise pattern by comparing a spectrum of recorded sound of a device of interest to a known noise pattern. The known pattern may be a pre-recorded and stored, either on a storage in the device of interest or on a remote server to which the device has access. The comparison can be done over the entire frequency range of the spectrum or over known noise regions, e.g., known, well defined, frequency regions where the type of blower usually exhibits a noise pattern when it is in a deteriorated state. This employs prior knowledge of the previous deterioration outcomes by capturing such sound and determining spectrums from known noisy blowers. To mitigate the gain effect of microphone (or other sensor) and eliminate the dependency on absolute numbers, both the pre-recorded and captured signals can be normalised. In one example, a peak value in the signal may be used as a normalisation factor for the recording.

As previously mentioned, there are different methods that may be implemented to compare the similarity of the two signals when comparing a spectrum of recorded sound of the device of interest to a known noise pattern to produce a score of similarity. One such method involving statistical correlation may apply a cross correlation function. The output of the cross-correlation function may then be compared to a predefined value which is chosen to be a threshold or limit for noisiness (noise threshold) of the blower for classification. If the cross correlation is high (significantly similar) such that it is higher than the limit, the output of the comparison may serve as a classification that the device of interest is potentially faulty. Similarly, if the comparison is less than the threshold, the classification may indicate that the device is not faulty. Optionally, the outcome of the comparison may also be presented as a percentage. If the result of the comparison is high, this may be nominated as 100%. Depending on the required noise (fault) and risk tolerance, one can choose the noise threshold to be a respective percentage of the 100% correlation (e.g., at least 80%). Then any spectrum, whether it covers a limited specific noise region or an entire frequency range, will itself be classified as noisy/faulty or otherwise, depending on whether its correlation with the known noisy spectrum is higher or lower than for example, 80%, respectively.

Optional step 8045 may derive a "noise vector" from one or more, any sub-combination, or all of the outputs or data sets from steps 8010, 8020, 8035 and/or 8040 (e.g., the harmonic peak ratios and optionally with their respective index (e.g., integer location) or alternatively as an ordered set of ratios to provide such an indication, the non-harmonic peak ratios such as with their respective non-integer multiples or corresponding location information, and/or the noise ratios). In one example implementation, the noise vector comprises a combination of the data sets of the harmonic peak ratios such as with location information, and the non-harmonic peak ratios such as with location information. In another example implementation, the noise vector comprises a combination of the data sets of the harmonic peak ratios such as with their respective index or as an ordered set, the non-harmonic peak ratios such as with their non-integer multiple, and the noise ratios. In another example implementation, the noise vector comprises a combination of the data sets of (a) either the harmonic peak ratios or the non-harmonic peak ratios, such as with respective location information, and (b) the noise ratios.

As noted above, the noise vector may contain peak ratios but may also include location information attributable to each particular peak ratio. For example, when the non-harmonic peak ratios are included in the vector, the vector may also include their respective non-integer multiple, such as a non-integer, so as to provide more than just the non-harmonic peak ratio but also where it is actually found. Similarly, when harmonic peak ratios are included in the noise vector, the vector may also include their respective integer multiple such as by an explicit inclusion of their index (which may be understood as the multiple of the motor speed). However, such respective integer multiple may instead be implicitly included when the noise vector contains the harmonic peak ratios as an ordered set so that the order that they are included or transmitted may be understood as location information (e.g., a first peak ratio of the noise vector may be understood to be a peak ratio at the motor speed, a second peak ratio of the noise vector may be understood to be at a peak ratio at two times the motor speed, and so on, etc.).

Step 8050 then applies a classifier to the noise vector to obtain a blower status indicator 8060.

As mentioned above, in some forms of the present technology, the step 8050 of the method 8000 may optionally be implemented by a controller of an external device such as the local external device 4288 or the remote external device 4286. In such forms, data representing the data set outputs of steps 8010, 8020, and/or 8040 (e.g., the harmonic peak ratios, the non-harmonic peak ratios, such as with their respective non-integer multiples, and the noise ratios) may be communicated to the external device via the local external communication network 4284 or the remote external communication network 4282 from the RT device 4000. In such forms, the step 8050 may be expressed as computer programs stored in a non-transitory computer readable storage medium accessible to the controller of the RT or RPT device or the controller of the external device (e.g., one or more processors of a server or other computer system, which is usually but not always remote to the RT or RPT device). Such programs configure the controller of the external device to execute the step 8050 to obtain the blower status indicator 8060. Thus, the central controller 4230 may optionally be configured to merely implement steps 8005 to 8040 by computer programs stored in a non-transitory computer readable storage medium of the RT device 4000, such as memory 4260. In such forms, the determined status indicator 8060 may be communicated to the central controller 4230 of the RT device 4000 via the local external communication network 4284 or the remote external communication network 4282.

As mentioned above, the classifier 8050 is configured to determine the status indicator 8060, such as from the derived noise vector, from the data set output(s) of any one or more of steps 8010, 8020, 8035, 8030 and/or 8040 (e.g., the harmonic peak ratios, the non-harmonic peak ratios and their respective non-integer multiples, spectra signature correlation(s), and/or the noise ratios). For example, the classifier may evaluate any of the data of the noise vector by one or more thresholds (e.g., by comparing the peak ratio(s) to one or more thresholds) to generate a status indicator.

Optionally, the status indicator 8060 may be continuously valued, e.g., a "blower noise score" expressed as a real number on some predetermined scale, or one of a set of discrete values, such as: {"OK", "needs service"}; {"green", "amber", "red"}; or an integer from 1 to 10 with 10 indicating the best condition. In either case, a series of status indicators 8060 may be generated and accumulated over time, and trends in the time series may be analysed to predict a future significant time, such as a date of failure or a date of next servicing.

In some implementations, the classifier 8050 may generate an output count such as by counting the number of harmonic peak ratios, and may compare the count to one or more threshold(s) (e.g., predetermined threshold(s) or a threshold), such as to determine if the count exceeds a predetermined threshold, to obtain the status indicator 8060. The thresholds may be the same or different for such comparisons with counts of the harmonic peaks ratios, non-harmonic-peak ratios and the noise region ratios (e.g., two, with one for each of the integer and non-integer peak ratios, and more than at least one for the noise regions). Similarly, the classifier may generate an output count that counts a number of significant signature correlations such as one or more correlation score above a value indicating similarity (e.g., a similarity threshold). The results of the count comparisons can be combined in an evaluation with an "or" function. For example, if any of the four indicators exceed a respective threshold (or respective threshold), the result of the evaluation can be taken as an indication of a blower with a potential problem. As discussed in more detail herein, further consideration of which of the specific indicator(s) exceeds the threshold, may also indicate a type of problem such as an identification of a problem with a specific component of the blower (e.g., a shaft, the ball bearings, the impeller, etc.).

Alternatively, or additionally, once the ratios are calculated, the classifier may combine them to derive a combined representative ratio number. For example, the classifier, or other pre-classification process, may optionally apply weight(s) to one or more of the ratios to determine weighted ratios, such as by multiplying such a ratio by a factor or weight factor, which may be different for the different ratios. For example, the factors or weight factors may be the same or different for the harmonic peak ratios, non-harmonic-peak ratios and the noise region ratios. All, or some plurality of, the ratios (e.g., the weighted ratio(s) [i.e., the ratios that have been multiplied by the factor(s)] and/or the unweighted ratio(s) [i.e., the ratios that have not been so multiplied by a factor]), may then be added to obtain a single number. Such a combined number may be considered a sum or weighted sum of the ratios. Such a sum may then be compared with a further threshold (a combination ratio threshold). The comparison may then provide an indication of blower status. For example, if the sum exceeds the combination threshold, the comparison may be taken as an indication of a blower with a potential fault. Giving different weight to one or more specific peaks may allow the process to focus on specific frequencies and frequency ranges of interest and ignore the effect of others that may not be relevant to potential issues with the blower. Thus, weight selection/application may allow more targeted diagnostic tests focusing on particular issues.

In some versions, in addition to or as a modification of the above implementation, the classifier 8050 may consider each of the harmonic peaks ratios, non-harmonic-peak ratios and the noise region ratios individually and extract information associated with each specific type of ratio. For example, the classifier may form a weighted or non-weighted sum from the harmonic peak ratios, such as by adding weighted (or non-weighted) values of the ratios to obtain a number characterising the harmonic peak ratios. Similar numbers may be obtained for each of the other two types of ratios (i.e., integer and non-integer) respectively such that the resulting numbers may be added together to form a single number indicative of each potential fault. This final addition may represent another weighted sum, where different weights may be given to the number representing each of the above three types of ratios. Thus, in some implementations one sum may be generated for any subset or for all of the modes, (e.g., a weighted sum for integer multiple peak ratios, another weighted sum for non-integer multiple peak ratios, and another weighted sum for the noisy region ratio or noise ratios.) These three sums may be evaluated individually, such as by comparing each to one or more thresholds, to identify a certain noise type and an associated noisiness level (e.g., integer peaks vs non integer peaks) within each category/mode. Additionally, or alternatively, they may all be combined to generate a single fine sum, which may be compared to one or more thresholds, to generate an overall noisiness categorisation.

In some implementations, the classifier 8050 may generate an output count such as by counting the number of harmonic and/or non-harmonic peak ratios in the noise vector. In some implementations, the classifier 8050 may be a more sophisticated structure such as a neural network to which the noise vector is applied to determine the blower status indicator.

In some implementations, and in particular those in which the classifier 8050 is a structure such as a neural network, the classifier 8050 may be previously trained using noise vectors obtained from blowers of known status using machine learning methods. The status may include different state of wear-off and/or defects with known components of the blower. In such implementations, the classifier 8050 applies thresholds and weights that have been obtained from its previous training to the noise vector to determine the status indicator 8060.

The determined blower status indicator 8060 may be communicated to a user of the RT device 4000 by the controller 4230. In one implementation, the controller 4230 may control an output presentation of, or based on, the determined status indicator 8060, such as to a user on a display. For example, the controller may convert the status indicator to a graphical representation, e.g. text characters, and display it on the display 4294 of the output device 4290 of the RT device 4000. Such a display may act as a prompt to the user to have the RT device 4000 serviced, or a reassurance that all is functioning correctly. In some implementations, a control operation of the blower or pressure generator may be set based on the status indicator. For example, the controller may disable or deactivate an operation of the motor of the blower based on a status indicator. By way of further example, the controller may limit operation of the motor of the blower based on a status indicator. For example, such a limit may prevent operation above (or below) a predetermined speed. Such a controller limit operation may also be applied with respect to a therapy parameter such as by the controller limiting operation to a particular target pressure, or particular target flow, that is set based on the status indicator. By so limiting the therapy parameters, the controller may serve to preserve or prolong operations of a potentially declining status of the blower while still maintaining a minimum necessary therapy. Furthermore, the controller may send data or a message to a remote computer (such as one belonging to the RPT device manufacturer, a medical practitioner, an HME etc.), such as to a remote external device and/or local external device via a communication interface 4280, for status verification or for notifying of the status of the blower.

The illustrated spectra, such as these in FIGS. 7A to 7C, the indicated recommended motor speeds, spectrum ranges and "quiet" regions, as well as the various threshold numbers discussed in the above text are specifically associated with a ResMed's AirSense 11 device. It is likely that other brand and/or model devices may exhibit some differences in the spectra and may require differently defined motor speeds, spectral power regions and comparison thresholds.

However, as discussed above, these can be identified relatively easily by running one or more of the specific type of devices having motor defects and monitoring the exhibited spectra and peaks and adjusting the speeds, spectral regions and thresholds used, correspondingly.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried, such as toward a patient end from a device end, by a pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried, such as from an RT device, by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

RPM: Revolutions per minute.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. Airway patency may be quantified, for example with a value of one (1) being open, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| patient | 1000 |
|---|---|
| bed partner | 1100 |
| patient interface | 3000 |
| seal - forming structure | 3100 |
| plenum chamber | 3200 |
| structure | 3300 |
| vent | 3400 |
| connection port | 3600 |
| forehead support | 3700 |
| RT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| mufflers | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| electrical components | 4200 |
| PCBA | 4202 |
| power supply | 4210 |

36

-continued

| input devices | 4220 |
|---|---|
| central controller | 4230 |
| clock | 4232 |
| therapy device controller | 4240 |
| protection circuits | 4250 |
| memory | 4260 |
| transducers | 4270 |
| pressure sensor | 4272 |
| flow rate sensor | 4274 |
| motor speed transducer | 4276 |
| microphone | 4278 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre - processing module | 4310 |
| interface pressure estimation | 4312 |
| vent flow rate estimation | 4314 |
| leak flow rate estimation | 4316 |
| respiratory flow rate estimation | 4318 |
| therapy engine module | 4320 |
| phase determination | 4321 |
| waveform determination | 4322 |
| ventilation determination | 4323 |
| inspiratory flow limitation determination | 4324 |
| apnea/hypopnea determination | 4325 |
| snore determination | 4326 |
| airway patency determination | 4327 |
| target ventilation determination | 4328 |
| therapy parameter determination algorithm | 4329 |
| therapy control module | 4330 |
| status determination module | 4340 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |
| spectrum | 7000 |
| spectrum | 7100 |
| peak | 7110 |
| peak | 7120 |
| peak | 7130 |
| spectrum | 7200 |
| method | 8000 |
| step | 8005 |
| step | 8010 |
| step | 8020 |
| step | 8030 |
| step | 8035 |
| step | 8040 |
| step | 8045 |
| step | 8050 |
| status indicator | 8060 |

The invention claimed is:

1. A respiratory therapy system for treating a respiratory disorder in a patient, the system comprising:
a pressure generator configured to generate a flow of air through an air circuit to a patient interface for treating the respiratory disorder, the pressure generator comprising a motor;
a transducer configured to generate a signal representing sound in the air circuit generated by the pressure generator during generation of the flow of air;
a controller configured to:
control the pressure generator to generate the flow of air;
compute a frequency domain representation of the generated sound signal;

process the frequency domain representation by performing one or more of:

(a) applying, to the frequency domain representation, an integer-multiple function of a fundamental frequency attributable to operation of the motor, (b) applying, to the frequency domain representation, a non-integer-multiple function of the fundamental frequency attributable to operation of the motor, (c) applying, to the frequency domain representation and one or more predetermined fault signature spectra, a statistical correlation function, and (d) applying, to the frequency domain representation, a resonant frequency function; and derive a noise vector with output data from the processing of the frequency domain representation; and a processor configured to:

classify the noise vector to obtain a status indicator of at least a component of the pressure generator; and generate an output based on the status indicator.

2. The system of claim 1, wherein the output data comprise values of peak ratios.

3. The system of claim 2, wherein the non-integer-multiple function is further configured to threshold peak ratios using one or more predetermined first ratio thresholds.

4. The system of claim 2, wherein the controller is configured to compute at least one peak ratio of the peak ratios by dividing a height of a peak by a power in a band surrounding the peak.

5. The system of claim 4, wherein the power is an average power or a root mean square (RMS) power.

6. The system of claim 1, wherein the controller is configured to apply the integer-multiple function and wherein the integer-multiple function is configured to extract harmonic peak ratios from peaks in the frequency domain representation at integer multiples of the fundamental frequency, and wherein the noise vector is derived, for the classifying, with output data from the applying of the integer-multiple function.

7. The system of claim 1, wherein the controller is configured to apply the non-integer-multiple function and wherein the non-integer-multiple function is configured to extract non-harmonic peak ratios from peaks in the frequency domain representation at non-integer multiples of the fundamental frequency, and wherein the noise vector is derived, for the classifying, with output data from the applying of the non-integer-multiple function.

8. The system of claim 7, wherein the non-integer-multiple function is further configured to output location information of the non-harmonic peak ratios.

9. The system of claim 1, wherein the controller is configured to apply, to the frequency domain representation, the resonant frequency function, and to derive the noise vector with output data from the resonant frequency function.

10. The system of claim 9, wherein the output data from the resonant frequency function comprises power data for one or more predetermined resonant regions.

11. The system of claim 10, wherein the power data comprises a noise ratio.

12. The system of claim 11, wherein the noise ratio comprises an average power of a predetermined resonant region divided by a power of a reference region.

13. The system of claim 1, wherein the processor is configured to:

access the one or more predetermined fault signature spectra; and apply, to the frequency domain representation and the one or more predetermined fault signature spectra, the statistical correlation function, wherein the noise vector is derived, for the classifying, with output data from the applying of the statistical correlation function.

14. The system of claim 13, wherein to classify the noise vector, the processor is configured to compare the output data from the applying of the statistical correlation function to one or more correlation thresholds.

15. The system of claim 1, wherein, to classify the noise vector, the processor is configured to count harmonic peak ratios in the noise vector that exceed one or more second predetermined thresholds.

16. The system of claim 1, wherein, to classify the noise vector, the processor is configured to form a weighted sum from harmonic peak ratios generated with the integer-multiple function.

17. The system of claim 1, wherein the processor is a processor of a computing device that is external to the controller, and wherein the controller is configured to communicate the noise vector to the processor.

18. The system of claim 17, wherein the output generated based on the status indicator comprises a communication of the status indicator to the controller.

19. The system of claim 1, wherein the output generated based on the status indicator comprises at least one of (a) a presentation on a remote display, and (b) sending a message or instruction to a device external to the controller and/or the processor.

20. The system of claim 1, wherein the controller is further configured to control operation of the pressure generator based on the status indicator.

21. The system of claim 20, wherein the controller is configured to deactivate the pressure generator based on the status indicator.

22. The system of claim 20, wherein the controller is configured to limit operation of the pressure generator based on the status indicator.

23. The system of claim 1, wherein the transducer is in, or in a fluid communication with, an air flow path of the pressure generator and/or the air circuit.

24. The system of claim 1, wherein the controller is configured to operate the transducer to generate the signal representing sound during the control of the pressure generator by the controller in a therapy mode.

25. The system of claim 24, wherein, for the computing of the frequency domain representation, the controller is configured to parse the signal representing sound into a plurality of intervals that each coincide with a period of time of a sub-portion of a respiratory event type.

26. The system of claim 25, wherein the respiratory event type comprises a detected apnea and/or a detected breath cycle.

27. The system of claim 25, wherein the period of time of the sub-portion of the respiratory event type comprises a detected interval coinciding with a predetermined blower motor speed that is approximately constant.

28. The system of claim 25, wherein the controller is configured to combine the parsed intervals for the computing of the frequency domain representation.

29. The system of claim 25, wherein the controller is configured to combine a number of the parsed intervals to at least achieve a minimum quantity.

30. The system of claim 29, wherein the minimum quantity comprises a breath count associated with the combined number of the parsed intervals or an accumulated time amount of the combined number of the parsed intervals.

31. The system of claim 1, wherein the classifier is configured to classify a weighed sum of integer multiple peak ratios, non-integer multiple peak ratios, and noise ratios.

32. The system of claim 1, wherein the classifier is configured to classify each of a weighed sum of integer multiple peak ratios, a weighted sum of non-integer multiple peak ratios, and a weighted sum of noise ratios.

33. A method of determining a status of a respiratory therapy system comprising a pressure generator for generating a flow of air through an air circuit to a patient interface, the method comprising:

generating with a transducer of the respiratory therapy system, a sound signal representing sound in the air circuit during generation of the flow of air;

computing a frequency domain representation of the sound signal;

processing, with one or more processors of the respiratory therapy system, the frequency domain representation by one or more of:

(a) applying, to the frequency domain representation, an integer-multiple function of a fundamental frequency attributable to operation of a motor of the pressure generator, (b) applying, to the frequency domain representation, a non-integer-multiple function of the fundamental frequency attributable to operation of the motor of the pressure generator, (c) applying, to the frequency domain representation and one or more predetermined fault signature spectra, a statistical correlation function, and (d) applying, to the frequency domain representation, a resonant frequency function;

deriving a noise vector with output data from the processing of the frequency domain representation;

classifying the noise vector to obtain a status indicator of at least a component of the pressure generator; and generating an output based on the status indicator.

34. The method of claim 33, wherein the output data comprises values of peak ratios.

35. The method of claim 34, wherein the method comprises the applying the non-integer-multiple function, wherein applying the non-integer-multiple function further comprises thresholding peak ratios using one or more predetermined first ratio thresholds.

36. The method of claim 33, wherein the processing comprises the applying the integer-multiple function, and wherein the integer-multiple function extracts harmonic peak ratios from peaks in the frequency domain representation at integer multiples of the fundamental frequency, and wherein the noise vector is derived, for the classifying, with output data from the applying the integer-multiple function.

37. The method of claim 33, wherein the processing comprises the applying the non-integer-multiple function, and wherein the non-integer-multiple function extracts non-harmonic peak ratios from peaks in the frequency domain representation at non-integer multiples of the fundamental frequency, and wherein the noise vector is derived, for the classifying, with output data from the applying the non-integer-multiple function.

38. The method of claim 37, wherein the non-integer multiple function identifies location information of the non-harmonic peak ratios.

39. The method of claim 37, wherein the processing comprises the applying of the resonant frequency function, and wherein the noise vector is derived with output data from the resonant frequency function.

40. The method of claim 39, wherein the output data from the resonant frequency function comprises power data for one or more predetermined resonant regions.

41. The method of claim 33, further comprising:

accessing one or more predetermined fault signature spectra; and applying, to the frequency domain representation and the one or more predetermined fault signature spectra, the statistical correlation function, wherein the noise vector is derived, for the classifying, with output data from the applying of the statistical correlation function.

42. The method of claim 33, wherein the classifying comprises counting harmonic peak ratios in the noise vector that exceed one or more second predetermined thresholds.

43. The method of claim 33, wherein the classifying comprises forming a weighted sum from harmonic peak ratios generated with the integer-multiple function.

44. The method of claim 33, further comprising controlling, by a controller, an operation of the pressure generator based on the status indicator.

45. The method of claim 33, wherein the transducer generates the sound signal during operation of the pressure generator in a therapy mode.

46. The method of claim 45, further comprising, for the computing of the frequency domain representation, parsing the sound signal into a plurality of intervals that each coincide with a period of time of a sub-portion of a respiratory event type.

47. The method of claim 46, wherein the classifying evaluates a weighed sum of integer multiple peak ratios, non-integer multiple peak ratios, and noise ratios.

* * * * *